US008522979B2

(12) United States Patent
Bennett et al.

(10) Patent No.: US 8,522,979 B2
(45) Date of Patent: Sep. 3, 2013

(54) RECOVERY OF REPROCESSABLE MEDICAL DEVICES IN A SHARPS CONTAINER

(75) Inventors: Gregg D. Bennett, Bellevue, WA (US); Michael S. Kovacs, Sammamish, WA (US)

(73) Assignee: Stericycle, Inc., Lake Forest, IL (US)

( * ) Notice: Subject to any disclaimer, the term of this patent is extended or adjusted under 35 U.S.C. 154(b) by 0 days.

(21) Appl. No.: 13/286,976

(22) Filed: Nov. 1, 2011

(65) Prior Publication Data

US 2012/0111770 A1    May 10, 2012

Related U.S. Application Data

(60) Continuation of application No. 12/547,722, filed on Aug. 26, 2009, now Pat. No. 8,061,528, which is a division of application No. 11/252,004, filed on Oct. 17, 2005, now Pat. No. 7,677,395, which is a continuation-in-part of application No. 10/943,586, filed on Sep. 17, 2004, now Pat. No. 7,591,380.

(51) Int. Cl.
*B07C 5/00* (2006.01)

(52) U.S. Cl.
USPC ......... 209/44.4; 209/44.1; 209/702; 209/703; 209/942

(58) Field of Classification Search
USPC ............... 209/44.1, 44.4, 552, 617, 630, 702, 209/703, 942
See application file for complete search history.

(56) References Cited

U.S. PATENT DOCUMENTS

| | | | |
|---|---|---|---|
| 4,867,384 A | 9/1989 | Waltert | 241/24 |
| 4,929,342 A | 5/1990 | Johnston | 209/12 |
| 5,064,124 A | 11/1991 | Chang | 241/33 |
| 5,205,417 A | 4/1993 | Herren | 209/630 |
| 5,249,690 A * | 10/1993 | Patterson | 209/630 |
| 5,454,000 A | 9/1995 | Dorfman | 714/54 |
| 5,508,004 A * | 4/1996 | Held et al. | 422/22 |
| 5,543,111 A | 8/1996 | Bridges et al. | 422/22 |
| 5,551,355 A | 9/1996 | Haines et al. | 110/242 |
| 5,676,255 A * | 10/1997 | Flowers | 209/2 |
| 5,833,922 A * | 11/1998 | Held et al. | 422/22 |
| 6,149,017 A | 11/2000 | Manka | 209/630 |

(Continued)

FOREIGN PATENT DOCUMENTS

| | | |
|---|---|---|
| JP | 2002355614 | 12/2002 |
| WO | WO 01/87719 | 11/2001 |

OTHER PUBLICATIONS

Office Communication issued in U.S. Appl. No. 10/943,586, dated Feb. 18, 2009.

(Continued)

*Primary Examiner* — Terrell Matthews

(57) ABSTRACT

Reprocessable medical devices that have been disposed of in a sharps container are recovered, disinfected or sterilized, sorted, and packed for reprocessing in a generally continuous process. In one embodiment, either a sharps container or at least a portion of its contents is successively and controllably conveyed, either manually or automatically, through a plurality of processing stations that are configured to perform different operations. The operations performed by the processing stations can include, for example, detecting and identifying contents, cleaning and disinfecting, opening the sharps containers, separating and sorting their contents, and disposal of contents that are non-reprocessable. Reprocessable medical devices can be sorted by type as they move along on a conveyor.

20 Claims, 15 Drawing Sheets

(56) References Cited

U.S. PATENT DOCUMENTS

| | | | |
|---|---|---|---|
| 6,779,668 B2 | 8/2004 | Nagler | 209/617 |
| 7,018,592 B2 | 3/2006 | Bowen | 422/295 |
| 7,103,023 B2 | 9/2006 | Sakakura | 370/331 |
| 7,119,689 B2 * | 10/2006 | Mallett et al. | 340/572.1 |
| 7,123,150 B2 | 10/2006 | Mallett et al. | 340/572.1 |
| 7,170,023 B1 | 1/2007 | Drake et al. | 209/584 |
| 7,303,081 B2 | 12/2007 | Mallett et al. | 209/702 |
| 7,591,380 B2 | 9/2009 | Bennett | 209/702 |
| 7,677,395 B2 | 3/2010 | Bennett et al. | 209/552 |
| 7,934,602 B2 | 5/2011 | Bennett | 209/702 |
| 7,984,810 B2 | 7/2011 | Bennett | 209/702 |
| 8,061,528 B2 | 11/2011 | Bennett et al. | 209/552 |
| 2003/0124025 A1 * | 7/2003 | Mize et al. | 422/28 |
| 2005/0065820 A1 | 3/2005 | Mallett et al. | 705/2 |
| 2005/0080520 A1 | 4/2005 | Kline et al. | 701/1 |
| 2005/0216369 A1 * | 9/2005 | Honegger | 705/28 |
| 2008/0195247 A1 * | 8/2008 | Mallett et al. | 700/225 |

OTHER PUBLICATIONS

Office Communication issued in U.S. Appl. No. 10/943,586, dated Jan. 31, 2008.

Office Communication issued in U.S. Appl. No. 10/943,586, dated Nov. 7, 2008.

Office Communication issued in U.S. Appl. No. 10/943,586, dated Nov. 13, 2007.

Office Communication issued in U.S. Appl. No. 11/252,004, dated Apr. 14, 2009.

Office Communication issued in U.S. Appl. No. 11/252,004, dated Oct. 22, 2008.

Office Communication issued in U.S. Appl. No. 11/252,004, dated Jun. 4, 2008.

Office Communication issued in U.S. Appl. No. 12/547,722, dated Mar. 22, 2011.

* cited by examiner

RECOVERY OF REPROCESSABLE MEDICAL DEVICES IN A SHARPS CONTAINER

RELATED APPLICATIONS

The present application is a continuation of Application No. 12/547,722 filed Aug. 26, 2009 now U.S. Pat. No. 8,061,528, which application is a divisional application based on prior application Ser. No. 11/252,004 filed Oct. 17, 2005, which is itself a continuation-in-part of patent application, Ser. No. 10/943,586, filed on Sep. 17, 2004, now U.S. Pat. No. 7,591,380, the benefit of the filing dates of which are hereby claimed under 35 U.S.C. §120.

BACKGROUND

Health care organizations are continually under pressure to find ways to lower or limit health care costs. One such opportunity for health care organizations to reduce costs is by recycling materials and supplies, in particular, by recovering single use medical devices (SUDs) that can be cleaned and sterilized for reuse, consistent with FDA regulations. Chapter 9 of the Federal Food, Drug and Cosmetic Act defines a medical device as an instrument, apparatus, implement, machine, contrivance, implant, in vitro reagent, or other similar or related article, including any component, part, or accessory, which is (1) recognized in the official National Formulary, or the United States Pharmacopeia, or any supplement to them, (2) intended for use in the diagnosis of disease or other conditions, or in the cure, mitigation, treatment, or prevention of disease, in man or other animals, or (3) intended to affect the structure or any function of the body of man or other animals, and which does not achieve its primary intended purposes through chemical action within or on the body of man or other animals and which is not dependent upon being metabolized for the achievement of its primary intended purposes.

For purposes of this patent application, medical devices fall into two categories. The first category is reusable devices, which are sold as reusable and can be cleaned and sterilized for reuse by a health care organization, such as a hospital, without regulatory approval. Reusable, manufacturer designated multiple-use medical devices are sold with the expectation the medical devices can and will be processed for reuse by hospitals or surgery centers within their own walls. Such medical devices are sold once and are typically cleaned and resterilized many times by the purchaser for use on multiple patients. These medical devices are collected after use by hospital or surgery center personnel and are cleaned, resterilized in an autoclave or by exposure to ethylene oxide or other appropriate sterilant, repackaged as necessary, and then reused in the same facility.

The second category is reprocessable devices, which are designated by the manufacturer for single use only or as disposable; these medical devices can legally be reused only if reprocessed consistent with FDA regulations. These SUDs are designated for only a single use, but many can, if properly cleaned and sterilized by a regulated process, be recycled for additional patient use. The FDA closely regulates the third party reprocessing industry that provides this service by requiring separate regulatory approvals for each device-type SUD to be reprocessed. An FDA approval (which is obtained through an FDA 510k application) for such devices is a premarket notification by the FDA that is issued in response to a party demonstrating that a medical device the party wants to sell/reprocess is as safe and effective as or substantially equivalent to an existing approved medical device that was or is currently on the United States market. Because hospitals do not have FDA 510k authorizations to reprocess SUDs, and because it does not appear that any hospital has applied for and received any FDA 510k authorizations to reprocess SUDs, a third party reprocessor industry has evolved with the engineering/regulatory infrastructure necessary to submit and receive multiple FDA 510k approvals, enabling these third parties to reprocess SUDs devices for the benefit of the medical industry.

Because medical devices are often "sharp" and used on patients in invasive procedures, strict requirements exist for their disposal after use. After use, such medical devices are unclean, often having been in contact with blood or other bodily fluids of a patient, but are still sharp. Indeed, many of these medical devices have a point or edge sharp enough to penetrate typical waste collection containers. Accordingly, hospital procedures require that a large proportion of such SUDs be disposed after use in a "sharps" container. Sharps containers are well known to those who work in medical care facilities and are intended to be used to collect potentially dangerous, used sharp medical devices that are capable of cutting or penetrating skin or penetrating a conventional waste package container. Typically, sharps containers contain a large volume of used syringes, needles, and broken glass. They also often contain used SUDs. These containers are periodically picked up from the facility by a regulated waste collector and transported to a central site for permanent destruction.

Traditionally, there are two ways medical care facilities contract for waste collection and management of sharps containers. Medical care facilities can purchase sharps containers intended for disposal in a variety of sizes, as needed, and appropriately provide the sharps containers inside patient rooms, laboratories, operating rooms, emergency rooms, etc. Medical care facilities personnel regularly monitor the status of individual sharps containers and collect them after they are full or after a predefined time period has elapsed. These containers are permanently "locked" at the point of collection, and a replacement empty sharps container is substituted for the full sharps container. Full sharps containers, which are permanently sealed and intended for disposal, are aggregated in a designated area for collection by a regulated medical waste hauler, who picks up the full sharps containers and transports them to a disposal plant. At the disposal plant, the sharps containers and their contents are then incinerated or otherwise completely destroyed without the containers ever being opened.

Alternatively, medical care facilities may choose to rent reusable sharps containers, rather than purchase sharps containers that are intended for disposal. At the disposal site, the lids of the reusable sharps containers are removed with a specially designed mechanical apparatus, and all of the contents are dumped directly into a waste disposal stream for immediate or near-immediate permanent disposal. The reusable sharps containers are then cleaned and disinfected and returned to a hospital or other medical care facility for reuse.

Although the reprocessing of SUDs is certainly more cost effective than the alternative of destruction, a study conducted in coordination with New York State environmental regulators determined that a very large number of potentially reprocessable SUDs were being disposed of in sharps containers and thus never reclaimed for reuse. In this study, sharps containers were accumulated from ten New York City hospitals for one week. Next, the sharps containers were forcibly opened, and the contents spread out on a stainless steel tray and sorted into two piles, including a pile of reprocessable SUDs, and a pile of all the other contents. Approximately twenty percent by volume of the contents of these containers were SUDs that, if properly reprocessed, could save the hospital approximately $1000 per sharps container. This figure equates to a savings of approximately $1,500 per hospital bed per year, or a $300,000 savings for a typical 200 bed hospital.

The foregoing examples of related art and limitations arising therein are intended to be illustrative and not exclusive. Other limitations of the related art will become apparent to those of ordinary skill in the art upon reviewing the disclosure that follows below.

SUMMARY

Recognizing a need to lower or at least limit medical care treatment costs, exemplary embodiments of a system for continuous recycling and reprocessing of SUDS were thus developed. One or more of these embodiments provide for directing a sharps container to a processing station to recover reprocessable medical devices within the sharps container, as well as separating out unusable medical devices and medical waste that should be destroyed.

One method for carrying out this process includes the steps of conveying the sharps container to the processing station to enable accessing the contents of the sharps containers and performing an operation on the sharps container at the processing station to recover the reprocessable medical devices from the sharps container. Either the sharps container or a portion of its contents may also be conveyed to a successive processing station where a processing step is performed that facilitates recovery of the reprocessable medical devices. An evaluation made at a processing station can determine whether the sharps container should be opened and whether at least a portion of its contents should be sorted, and processed for reuse, or be destroyed. Exemplary operations performed at a processing station include at least one of detecting the contents of the sharps container; weighing the sharps container; sterilizing either the sharps container or at least a portion of the contents of the sharps container; cleaning the sharps container or at least the portion of the contents of the sharps container; disinfecting the sharps container or at least the portion of the contents of the sharps container; emptying the contents of the sharps container onto a sorting surface; removing a reprocessable medical device from the contents of the sharps container; sorting the sharps containers into different groups based on the contents of the sharps containers; and identifying the reprocessable medical devices that can be processed for reuse to facilitate separating the reprocessable medical devices from the unusable medical devices and medical waste.

Another embodiment is directed to a system that includes a processing station configured to perform an operation on either a sharps container or a portion of its contents, within the processing station. The operation facilitates recovery of reprocessable medical devices from the sharps container. Also included is a conveyor configured to controllably convey either a sharps container or the portion of the contents of the sharps container along a route directed either into or out of the processing station. A sensor is provided to sense when the sharps container or the portion of the contents of the sharps container are disposed at a predefined location within the processing station such that an operation can be performed or to determine that an operation performed by the processing station is completed.

A memory that stores machine instructions and a controller coupled to the sensor and the memory are also included. The controller executes the machine instructions stored in the memory such that at least one of several exemplary functions is carried out. For example, the machine instructions can stop, start or pause the conveyor, the speed of the conveyor can be increased or decreased, the sharps container or the portion of the contents of the sharps container can be transferred to a different conveyor, a route can be selected along which the sharps container or the portion of the contents of the sharps container will be directed, or the operation on the sharps container or at least a portion of its contents can be performed.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein.

Figure 12:
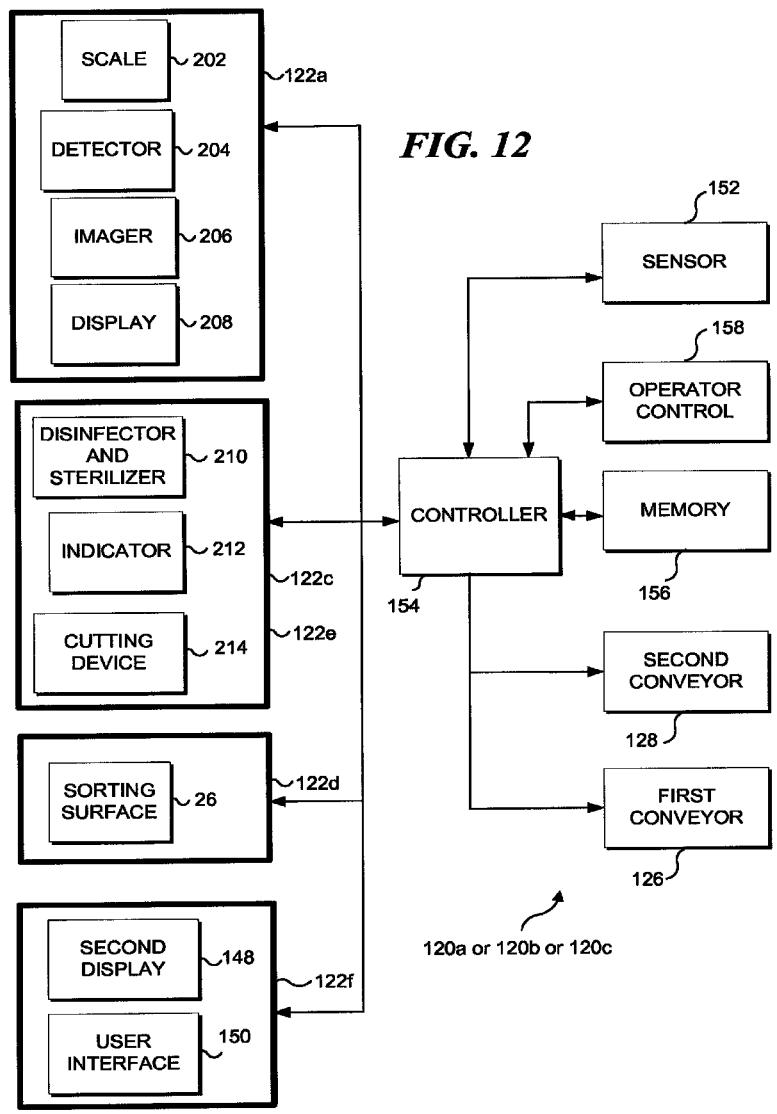
Figure 13:
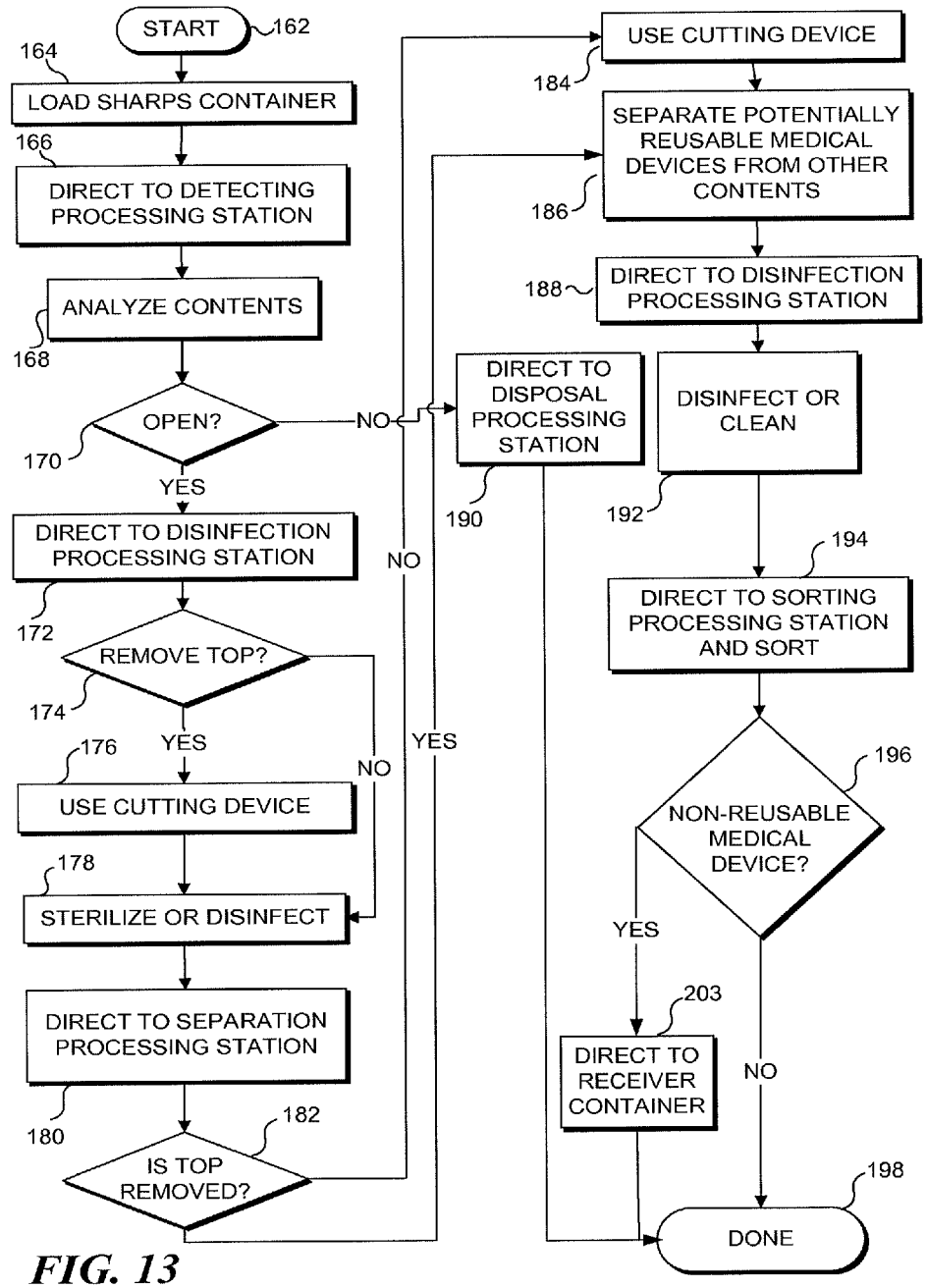

FIG. 12 is a schematic block diagram of the recovery processing system showing additional components included in a processing station; and FIG. 13 is a block diagram showing the steps followed in the present invention to separate reprocessable medical devices from non-reprocessable medical devices and medical waste that are contained in a sharps container in the continuous recovery processing system.

DESCRIPTION

Figures and Disclosed Embodiments are not Limiting

Exemplary embodiments are illustrated in referenced Figures of the drawings. It is intended that the embodiments and Figures disclosed herein are to be considered illustrative rather than restrictive.

The exemplary embodiments provide a safe and efficient method, apparatus, and continuous system whereby a sharps container whose contents would otherwise be incinerated or permanently disposed of, can be opened and sorted to separate SUDs that can be cleaned and sterilized for use from all other medical waste that should be destroyed. This processing of sharps containers can be carried out on a continuous basis by employing a convey system to convey either the sharps containers or at least portions of their contents to one or more processing stations. A sharps container is a basic container that is well known in the medical arts, for disposal of items that may have a sharp edge or point that is capable of cutting or piercing. The sharps container is typically made of a relatively hard plastic so that these used medical devices are safely contained within the sharps container and therefore not likely to penetrate the sides of the container, which could injure and/or transmit biohazard contaminants to people.

Sharps containers are generally intended to contain items such as hypodermic needles, syringes (both with and without needles attached), scalpels, pipettes, blood vials, broken glassware such as flasks, beakers, and specimen tubes, culture dishes, IV tubing, IV bags contaminated with visible blood, and dental wires. These medical devices are non-reprocessable and are properly intended to be permanently disposed of, usually by incineration. However, in addition to these properly non-reprocessable medical items, the sharps container may also include medical devices that are suitable for cleaning and reuse, such as trocars, laparoscopic and endoscopic devices, cutters, staplers, graspers, harmonic scalpels, burrs, blades, oxisensors, compression sleeves, catheters, bits, and saws. The cost of replacing these potentially reprocessable medical devices with new medical devices is substantially greater than the cost of cleaning and sterilizing the improperly discarded medical devices, so that they can be reused. It is unfortunate that through inadvertence and negligence, potentially reprocessable medical devices are placed into sharps containers to be destroyed rather than reused. In contrast, the following discussion recognizes that sharps containers may indeed include reprocessable medical devices and explains how the contents of a sharps container may safely be evaluated and efficiently sorted to recover the reprocessable medical devices, while any remaining non-reprocessable medical devices and other medical wastes are discarded, to be destroyed.

The result of this efficient sorting is that certain medical devices that have been used in a medical procedure at a medical care treatment facility and disposed of in a sharps container, may be recovered from the sharps container, cleaned, sterilized, repackaged, and reused by the medical care treatment facility. This recovery of reprocessable medical devices helps to lower or at least limit medical treatment care costs, especially considering the potential for certain medical devices to be reused multiple times.

The term "medical care treatment facility" is not intended to in anyway be limiting on the types of facilities that can be a source of the sharps containers that are processed with this invention. This term, without limitation, is intended to include hospitals, outpatient clinics, physicians' offices, nursing homes, medical clinics, dentists offices, blood banks, medical research facilities, laboratories, and any other facilities where medical devices are used that might be disposed of in a sharps container.

Recovery Processing Station

Figure 1:
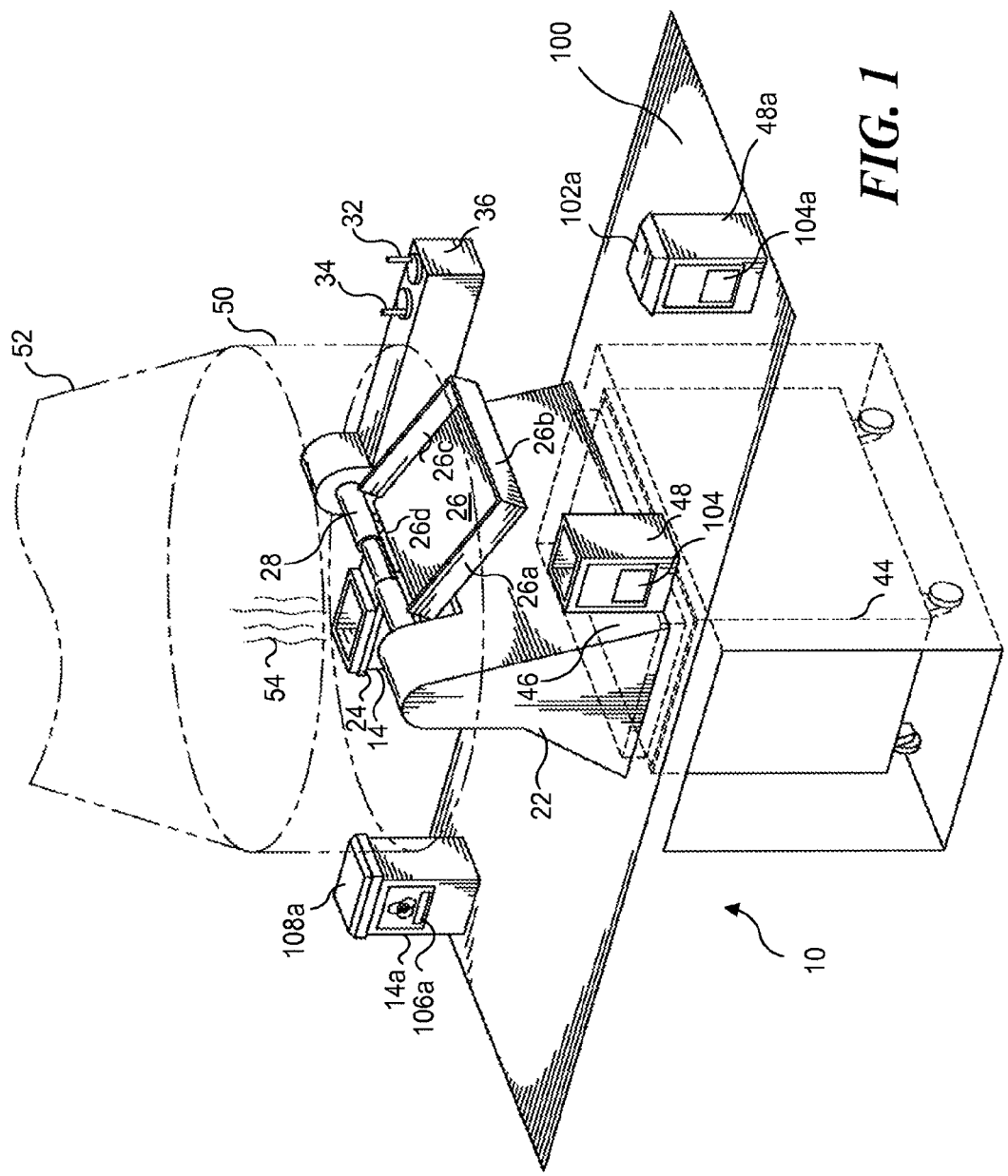
FIG. 1 is an overall isometric view of an exemplary embodiment of the present invention that is used to separate SUDs that can be cleaned and reused from all other medical waste that should be destroyed, where SUDs are contained in a sharps container.

FIG. 1 is an isometric view of a exemplary embodiment of a recovery device 10 that is usable as one processing station to sort the contents 12 (none of which are shown in this Figure) of a sharps container 14, to recover reprocessable medical devices (including those designated for multiple use and those designated as being reprocessable if processed by FDA approved agencies), leaving non-reprocessable medical devices and other medical waste that can then properly be disposed of permanently. Although the recovery device is not illustrated in use as part of a larger system, it will be apparent that it can be included and that various aspects of its operation can be automated so that the processing of multiple sharps container can be efficiently carried out in a more continuous fashion, rather than simply processing a single sharps container at a time.

The recovery device includes a frame 22, brackets 24, and a sorting surface 26.

Frame 22 supports brackets 24 and sorting surface 26, both of which are movable about an axis 28 when actuated by an electrical prime mover or manually. Sharps container 14 is removably attached to brackets 24 by a latch (not shown). The brackets are mounted to rotate about axis 28 at a fixed distance such that once the left and right edges of the sharps container are aligned with the edges on the brackets, the sharps container may be slid into slots formed in the brackets and the latch then fastened. The latch ensures that the sharps container is secured to the brackets so that the sharps container can be securely rotated about axis 28.

Those skilled in the art will recognize that alternatives exist for both the brackets and latch. For example, clamps (not shown) could be used instead of the latch to hold the sharps container in place on the brackets. Also, plates (not shown) could be used to support the bottom and sides of the sharps container, which could be secured to the plates by one or more straps or other type of hold down or clamping device.

It will also be understood that either an electric motor or a hand-powered crank can alternatively be employed to drivingly rotate the sorting surface and the sharps container about axis 28, to any desired orientation. For example, the sharps container can be tipped sufficiently to enable any liquid contained in the sharps container to drain into a waste receptacle 44, and when positioned in a fully inverted orientation, the contents of the sharps container will be dumped onto the sorting surface. Although illustrated in FIG. 1 as an enclosed gear box 36 that includes a transmission for rotating sorting surface 26 about axis 28, and then rotating both sorting surface 26 and sharps container 14 about axis 28, it will be understood that in this embodiment, a hand crank 32 and a main crank 34 are used for manually applying the rotary motion conveyed through gear box 36 to rotate the sharps container and the sorting surface about axis 28. Hand crank 32 is cranked to manipulate the sorting surface to rotate about axis 28, while main crank 34 is cranked to manipulate the sharps container to rotate about axis 28.

However, those skilled in the art will recognize that manipulation of the sharps container and the sorting surface about axis 28 may be accomplished without the hand crank and the main crank. For example, as shown in FIG. 1, the enclosed gear box 36 may manipulate the sorting surface and the sharps container to rotate about axis 28 when driven by one or more electric motors that are controlled by the operator moving hand crank 32 and main crank 34, i.e., where the two cranks are simply control handles that actuate switches or even determine the speed of rotation applied by the one or more electric motors. The details of the drive system for rotating the sharps container and the sorting surface are not important in regard to practicing this invention, and those of ordinary skill will understand that the rotator motion may be applied and controlled in many different ways.

In an exemplary embodiment, sorting surface 26 includes a side 26a, a side 26b, and a side 26c, with an open fourth side 26d. This open side enables any liquid in the sharps container to be drained into waste receptacle 44 after the reprocessable medical devices have been removed from the sorting surface. Open side 26d of the sorting surface also enables the non-reprocessable medical devices and the other medical waste to be deposited into waste bin 44 after all of the reprocessable medical devices have been removed from the sorting surface. Side 26a, side 26b, and side 26c of the sorting surface should also be of a height sufficient so that when the contents of the sharps container are dumped onto the sorting surface, the contents will not spill over the sides of the sorting surface. As an alternative, the sorting surface might include small perforations, similar to a grating, such that when the sorting surface and the sharps container are inverted, any liquid contents will drain through the perforations and into waste receptacle 44. The perforations should be sized to enable any liquid contents to drain yet prevent any solid contents of the sharps container from passing through the perforations.

Those skilled in the art will realize that although the sorting surface is shown in a square-shaped configuration, the shape of the sorting surface may vary as desired, so long as the size is sufficient to cover the opening formed when the lid of the sharps container is removed.

The sorting surface must be rotatably movable about axis 28, and is preferably readily removable, such that it can be periodically cleaned, disinfected, and repaired. In addition, although not shown in FIG. 1, in an alternative embodiment, the sorting surface may include protrusions such that when it is lowered onto the sharps container, the protrusions engage the walls of the sharps container in a clasped- or detent-like manner, thereby enabling the sorting surface and the sharps container to move together as either is rotated about axis 28. In contrast, the exemplary embodiment first discussed above uses the hand crank to lock the sorting surface into position or disengage it from the sharps container, such that the main crank manipulates the combined sharps container and sorting surface about axis 28.

Frame 22 is preferably partially enclosed to ensure that the non-reprocessable medical devices and the other medical waste are directed towards waste bin 44 and do not readily escape onto the outer surface of the recovery device or onto a platform 100 surrounding the recovery device. However, at least a frame opening 46 is provided in platform 100 for enabling the remaining sorted waste materials and non-reprocessable medical devices (and any liquid in the sharps container to drop into waste bin 44. This frame opening must be sized such that the non-reprocessable medical devices and the other medical waste can fall freely through the opening under the force of gravity. Thus, waste bin 44 is positioned under the frame to receive the non-reprocessable medical devices and the other medical waste, so that these items can be permanently destroyed.

In addition, frame 22 also includes a support for receptacle bin 48 that will receive the reprocessable medical devices removed by the operator from sorting surface 26. The receptacle bin is preferably disposed adjacent to the operator such that reprocessable medical devices may be speedily, safely, and efficiently transferred from the sorting surface to the receptacle bin for subsequent cleaning and sterilization.

Optional recovery device components that will ensure human safety and thus reduce exposure to biohazards include protective clothing (not shown) that is worn by the operator (including, optionally, a face mask with a supply of clean air), a shield 50 that overhangs the sharps container when initially fitted into the recovery device and the sorting surface, a vent 52, through which air from around and above the sorting surface is drawn, and a high-efficiency particulate arresting (HEPA) filter (not shown) that filters the air before it is exhausted to the outdoor ambient environment, so that any harmful pathogens are removed from the exhaust air. The operator will likely be garbed in protective gear in order to minimize contact with the sharps container biological and chemical contaminants. In addition, shield 50 will reduce the possibility of the operator being exposed to air-borne pathogens or aerosolized bio-contaminants or chemicals, as the sorting surface and sharps container are manipulated to rotate about axis 28 or while the operator is manually removing reprocessable medical devices from the sorting surface. Vent 52 also ensures that any pathogens or aerosolized harmful liquids in the sharps container such as fumes 54 are safely drawn away from the vicinity of the operator's working space.

Although an exemplary embodiment only provides for the sorting of one sharps container at a time, those skilled in the art will recognize that the recovery device could be designed so that a plurality of sharps containers might be processed at one time to recover reprocessable medical devices for cleaning and sterilization.

Method of Use

Figure 2:
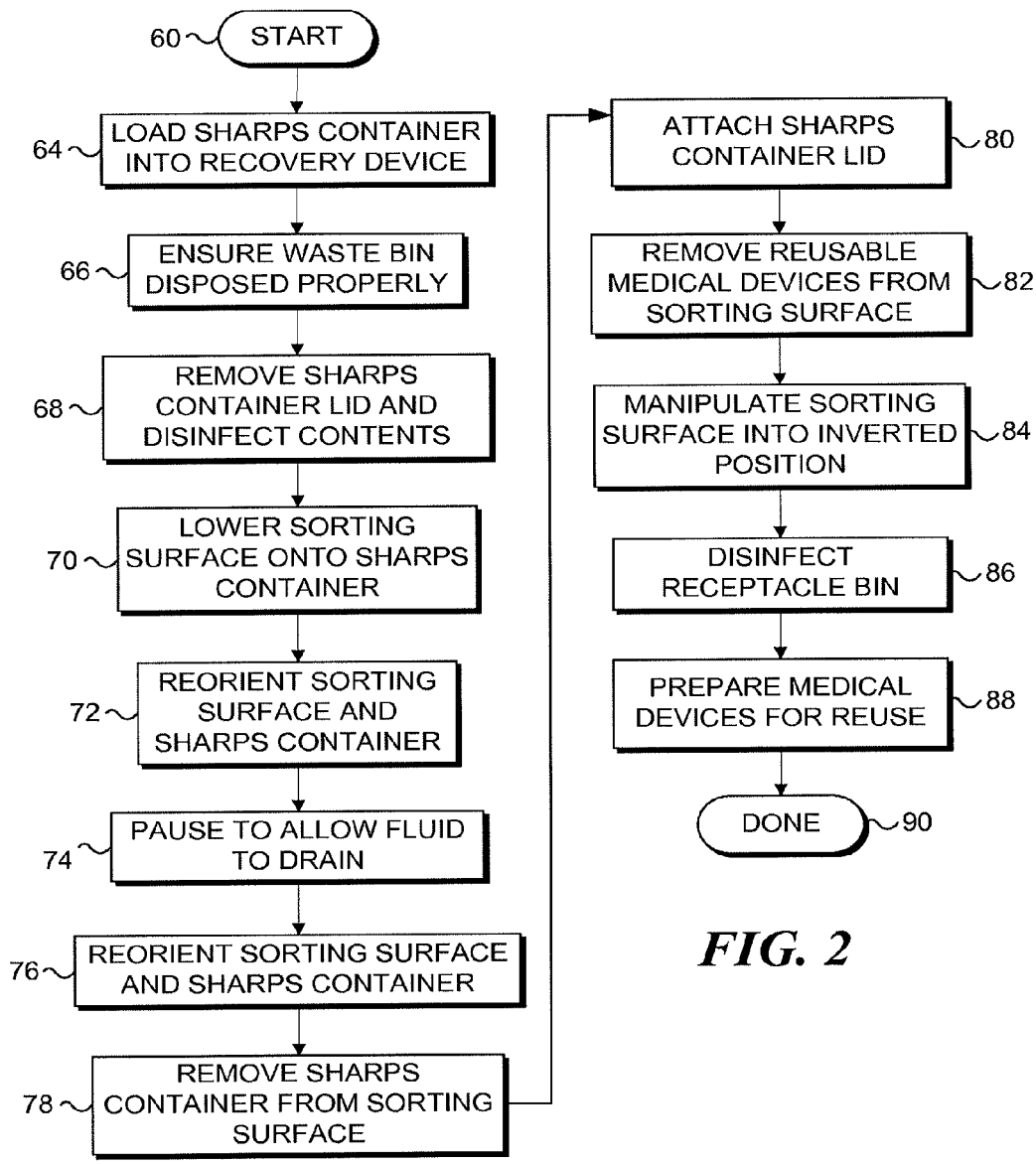
FIG. 2 is a block diagram showing the steps followed in the present invention to separate reprocessable medical devices from non-reprocessable medical devices that are contained in a sharps container.

FIG. 2 illustrates the logical steps implemented in connection with carrying out the method of the exemplary embodiment. It is very likely that operators at a recovery device center will be working with numerous sharps containers obtained from a number of medical care treatment facilities and other sources. Accordingly, the receptacle bin in which reprocessable medical devices are placed by the operator may be labeled appropriately with the name of the medical care treatment facility and/or department that is the source of the sharps container(s) from which the reprocessable medical devices placed in the recovery bin are derived. This information may be available on the label on the outside of the sharps container. Similarly, a label may be applied to the receptacle bin with the name and department of the medical care treatment facility that is the source of the sharps container being sorted.

From a start step 60, a step 64 provides for loading the sharps container into the recovery device and securing it therein with the latch. A step 66 indicates that the operator should check that the waste bin is properly disposed underneath the opening in the frame so that all non-reprocessable medical devices and the other medical waste can be disposed of properly once the contents of the sharps container have been sorted to recover any reprocessable medical devices (and to receive any liquid contents of the sharps container). A step 68 provides for removing the lid of the sharps container and disinfecting the total contents by thoroughly spraying the interior and contents with a disinfectant spray. All visible surfaces should be sprayed with the disinfectant until moist. The lid is removed by lifting one end and sliding it clear of the sharps container (or as otherwise appropriate for the design of the sharps container being processed). Removing the lid of the sharps container only after the sharps container is in the recovery device ensures that the benefits described above in connection with the operator protective clothing, the shield, the vent, and the HEPA filter are achieved.

In a step 70, the sorting surface is lowered onto the sharps container in response to the operator turning the hand crank. The sorting surface is then held in place over the open top of the sharps container by the force applied with the hand crank, while the main crank is engaged by the operator to control the rotation of the sorting surface and the sharps container as a unit. Alternatively, the sorting surface can be held in place by the protrusions (not shown) that secure it to the walls of the sharps container, as described above. However, there will be some nominal clearance between the sorting surface and the sharps container so that there is not a complete seal between the sorting surface and the sharps container in order for the liquid contents to drain from the sharps container and into the waste bin when the sharps container is rotated sufficiently to partially invert the sharps container.

At this point, in a step 72, the main crank is utilized to reorient the sorting surface and the sharps container such that at a step 74, the operator can pause the combination sufficiently long to enable any liquid contents to drain through the clearance opening between the sorting surface and the open top of the sharps container. The operator, in a step 76, then reorients the sorting surface and the sharps container such that the sharps container is substantially fully inverted relative to its original position.

A step 78 then provides for removing the sharps container from the sorting surface using the main crank. At this point, the entire contents of the sharps container, less the bulk of the liquid contents, should be deposited onto the sorting surface. If any medical waste or medical device still remains within the sharps container, the operator can pause with the sharps container still partially inverted over the sorting surface and rap the sides of the sharps container, causing the remaining medical waste or medical device to fall on the sorting surface. Or, the operator may need to reach inside the partially inverted sharps container with tongs or other suitable instrument to grasp the medical waste or medical device remaining inside and deposit it on the sorting surface.

A step 80 provides for reattaching the sharps container lid and placing the empty sharps container into a queue for cleaning and sterilization, so that the sharps container can be recycled and returned to the medical care treatment facility for future use. A step 82 indicates that the operator then removes all reprocessable medical devices from the sorting surface. The operator may remove the reprocessable medical devices using tongs or any kind of device that enables the operator to firmly grasp the reprocessable medical device and safely place it into the receptacle bin. Only those medical devices that are deemed reprocessable or federally regulated so that only licensed agencies can process them for reuse will be removed from the sorting surface and placed into the receptacle bin.

In a step 84, after all reprocessable medical devices have been removed from the contents on the sorting surface, the operator rotates the sorting surface into an inverted position using the hand crank so that the non-reprocessable medical devices and remaining medical wastes are caused to slide from the sorting surface and drop down into the waste bin. At this point, it may be necessary for the operator to remove any non-reprocessable medical devices from the sorting surfaces manually using the tongs or similar implement if the non-reprocessable medical devices and medical waste clings to the sorting surface and does not readily drop into the waste bin.

A step 86 then provides for disinfecting the receptacle bin (once it is full or once all of the sharps containers from a given medical treatment facility have been processed to place their reprocessable medical devices into the receptacle bin). This receptacle bin may then be shipped to an outside facility, as noted in a step 88, where the reprocessable medical devices will be processed for reuse, which includes cleaning, sterilizing, and repackaging, or alternatively, the receptacle bin will remain at the recovery device center for similar processing. At this point, the recovery process is completed as indicated in a step 90.

Figure 3:
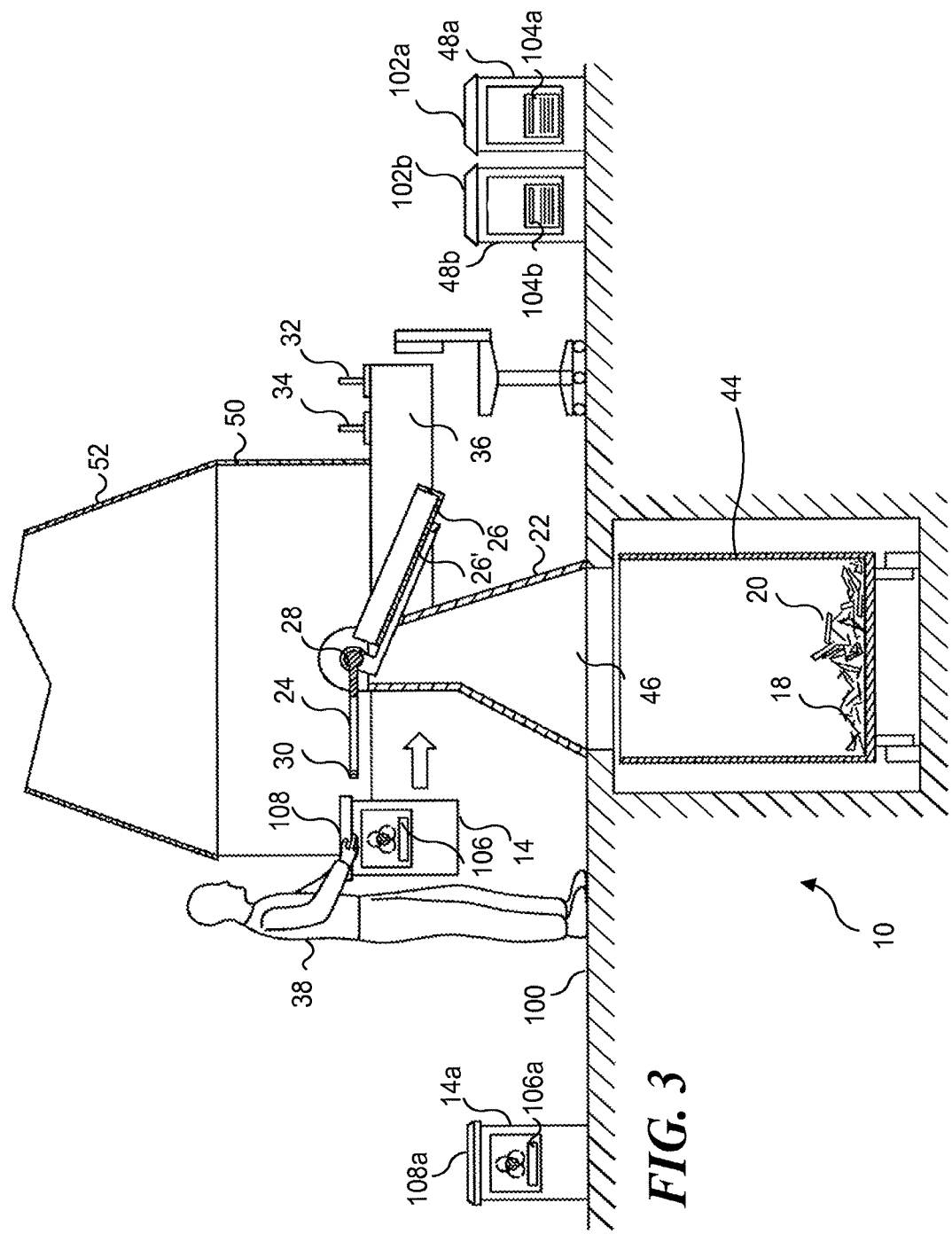
FIG. 3 is a schematic plan view of a sharps container being loaded into the recovery device at the beginning of a sorting cycle that enables an operator to separate reprocessable medical devices from non-reprocessable medical devices.

FIGS. 3-9 illustrate the various steps of the method discussed above. For example, FIG. 3 illustrates a sharps container 14 as it is about to be loaded into the recovery device by an operator 38 who stands on platform 100; another sharps container 14a is in the sorting queue and is next to be processed. This Figure also illustrates the cyclical nature of the sorting routine performed by the recovery device, since it shows sealed receptacle bins 48a and 48b that are in the queue for post sorting processing. A lid 102a and a lid 102b are secured on receptacle bin 48a and receptacle bin 48b, respectively, and thus indicate that they contain reprocessable medical devices that have already been recovered by sorting through the contents of one or more sharps container and are ready for post sorting cleaning, sterilization, and packaging, and the value will be allocated to the appropriate medical facility and department as indicated on a label 104a and a label 104b, respectively. Waste bin 44 is partially full of non-reprocessable medical devices 18 and other medical waste 20 from earlier sorting of sharps containers. Once waste bin 44 is full, it will be removed, the contents destroyed, the waste bin will be cleaned and sanitized. An empty waste bin will then be disposed beneath the recovery device.

Although platform 100 is shown in all the Figures, those skilled in the art will realize that frame 22 can be easily designed in an alternative configuration such that it completely encloses the waste bin, which is removable by opening an access panel. Therefore, operator 38 does not need to stand on the platform in this alternative embodiment in order to manipulate the recovery device and sort through the contents of the sharps container.

Prior to being loaded into recovery device 10, as described above, the label on the sharps container may have been noted and the receptacle bins may be labeled to indicate the source of the recovered reprocessable medical devices sorted from the contents of the sharps container, based upon the label of the sharps container. For example, a label 106a on a sharps container 14a might be appropriately labeled, "Caution, Biohazard, Infectious Waste, Metropolis City Hospital—Heart Surgery Department." Similarly, the label on the receptacle bin that will be used to receive the reprocessable medical devices sorted from the contents of sharps container 14a may be labeled to indicate that the source of the reprocessable medical devices contained therein is the Metropolis City Hospital—Heart Surgery Department.

Operator 38, who is garbed in protective gear (not shown), is illustrated securely mounting sharps container 14 into recovery device 10 by sliding the edges of the sharps container onto brackets 24 and securing it in place with a latch 30. A lid 108 of the sharps container is still secured to sharps container 14 that is being mounted onto the brackets. Notice that a lid 108*a* is still secured to sharps container 14*a* that will be sorted after sharps container 14 has been sorted.

Figure 4:
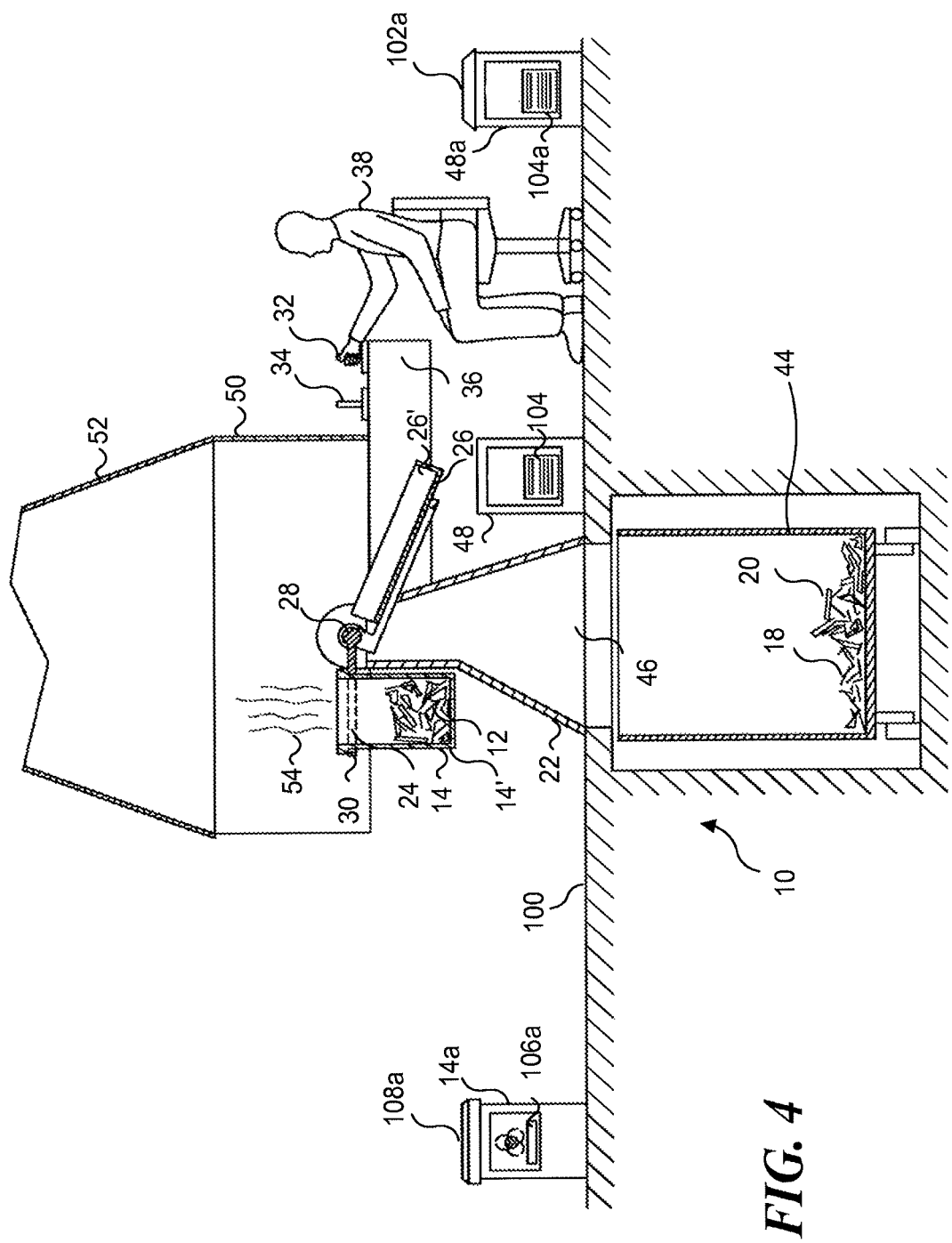
FIG. 4 is a schematic plan view of an operator manipulating the sorting surface over an opening in a sharps container that has been loaded into the recovery device.

In FIG. 4, sharps container 14 is shown after it has been mounted to brackets 24 and fastened upright in the recovery device. Although this step is not shown, operator 38 has removed the lid from sharps container 14 by lifting and sliding it clear of the sharps container, as is evident by fumes 54 that are wafting up from contents 12 of the sharps container. The operator has set lid off to the side and it is not shown in this Figure. At this point, operator 38 sprays the contents of sharps container 14 with a disinfectant. This disinfectant should cover and wet all surfaces of the contents and the interior of sharps container 14 that are visible, including all surfaces of reprocessable medical devices, non-reprocessable medical devices, and other medical waste until all these items are visibly moist. Vent 52 and the HEPA filter (not shown) are then used to draw any pathogens and aerosolized bio-contaminants up and out of the region under shield 50, so that operator 38 may work in as safe an environment as possible. At this point, operator 38 begins to change the orientation of the sorting surface.

Figure 5:
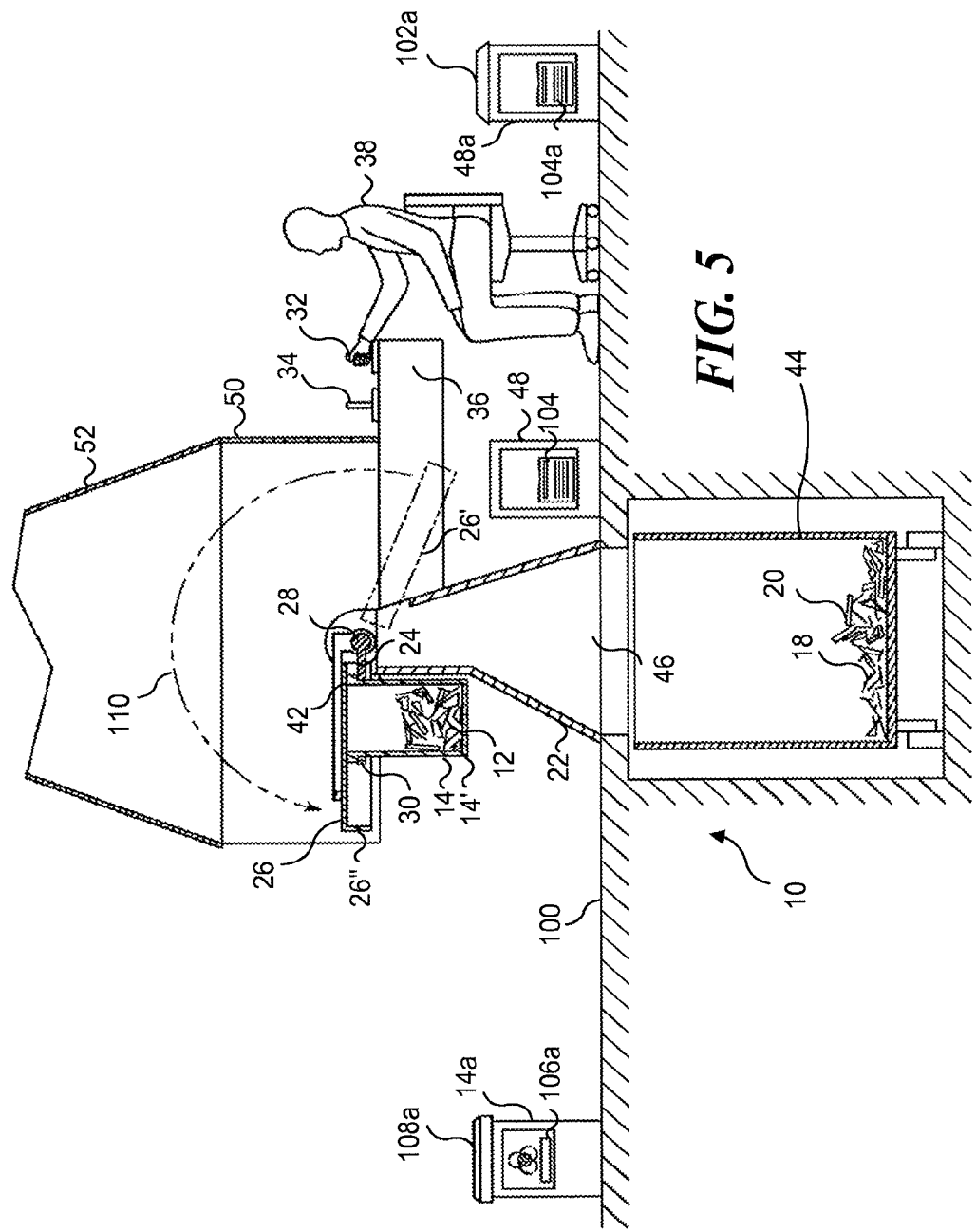
FIG. 5 is a schematic plan view showing how the operator manipulates the recovery device so that the sorting surface is rotated about an axis to be disposed atop the sharps container.

In this exemplary embodiment, the two cranks are manually activated by the operator to change the orientation of sorting surface 26 and then the combined sorting surface and sharps container 14. Activation of hand crank 32 on the recovery device enables sorting surface 26 to be rotated from an initial position 26', as shown in FIG. 4, and lowered onto the open top of sharps container 14 into a position 26", as shown in FIG. 5. As illustrated in FIG. 5, the range of rotational movement of the sorting surface is indicated by an arc 110, as sorting surface 26 is rotated about axis 28 from its initial position 26' by the operator turning hand crank 32, until sorting surface 26 rests on top of sharps container 14 in position 26". Note that sorting surface 26 is sized such that it covers the entire open top of sharps container 14. Although it is not shown, the sorting surface may have protrusions on its surface so that when the sorting surface is lowered onto the sharps container, the protrusions engage the walls of the sharps container. Alternatively, the hand crank disengages from acting upon the sorting surface and simply holds the sorting surface into contact with the top of the sharps container, once the sorting surface rests atop the sharps container, so that main crank 34 rotates both the sharps container and the sorting surface when actuated by the operator.

However, regardless of the method that is used to ensure that the sorting surface and the sharps container are temporarily engaged, the sorting surface is positioned or aligned over the sharps container so that when the contents are upended onto the sorting surface, there is no spillage of the contents of the sharps container over the sides of the sorting surface.

Figure 6:
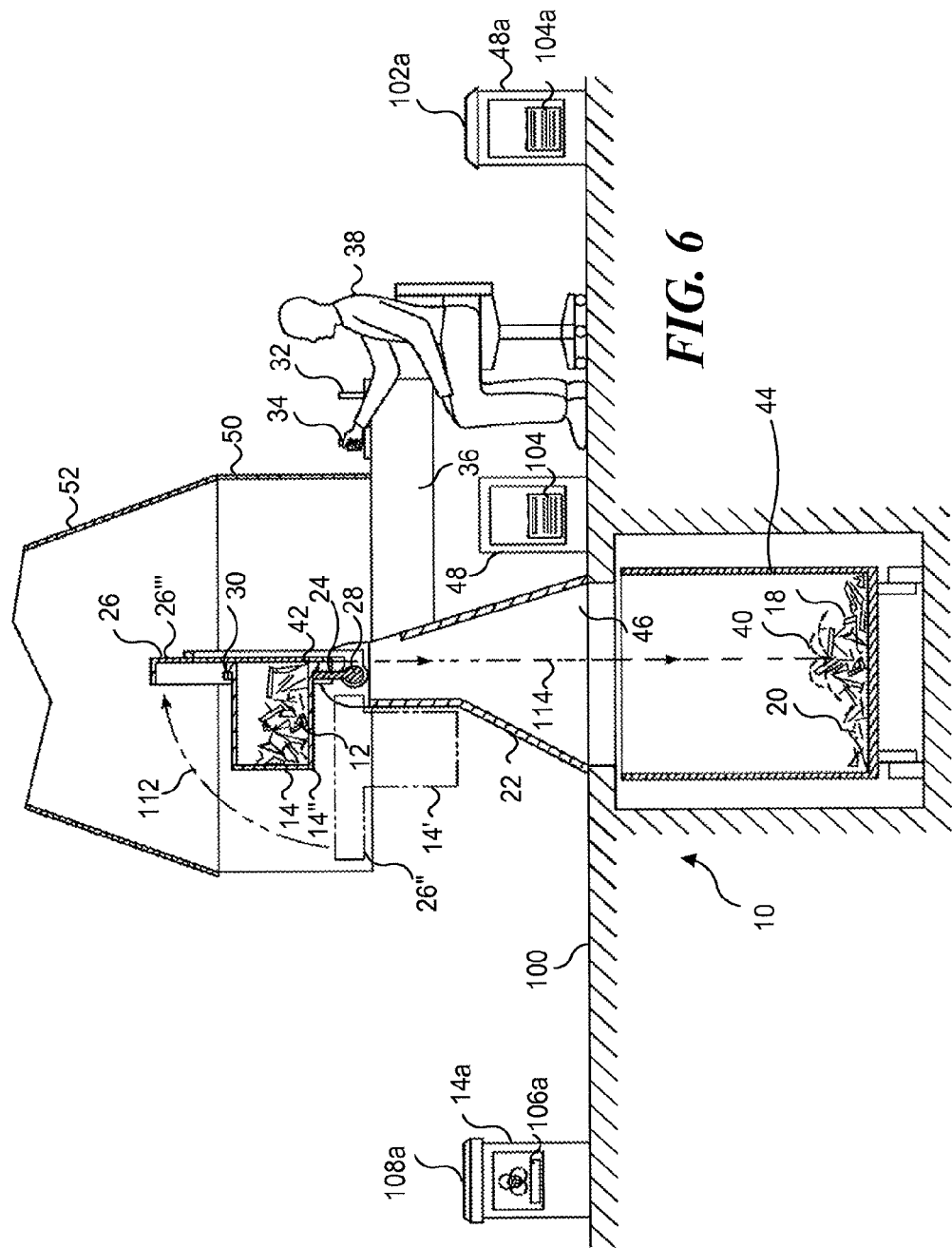
FIG. 6 is a schematic plan view showing how the operator manipulates both the sharps container and the sorting surface into a partially inverted position such that any liquid contents may be drained from the sharps container prior to emptying its contents for sorting.

With reference to FIG. 6, operator 38 is shown activating main crank 34 so that sharps container 14 and sorting surface 26 are rotating from positions 14' and 26", respectively, about axis 28 through an arc 112, to inverted positions, position 14" and position 26''', respectively. The purpose of partially inverting the sharps container and the sorting surface is to enable any liquid contents 40 within the sharps container to drain through opening 42 and into waste bin 44 through frame opening 46, as indicated by dash line 114. The liquid contents may also include blood, intravenous fluids, and residual chemicals from specimen tubes, flasks, and beakers, and any residual disinfectant. The waste bin is disposed immediately below frame 22 so that it will receive liquid contents 40 as they fall onto non-reprocessable medical devices 18 and other medical waste 20 from previously processed sharps containers. As described above, the recovery device cycles through multiple sharps containers, and it is likely that the waste bin will be used for multiple cycles of processing sharps containers until the waste bin becomes full.

Those skilled in the art will notice that although partially inverted positions, position 14" and position 26''' appear to form an angle slightly greater than 90° relative to position 14' and position 26", so that the opening into the sharps container is at its lowest point, various greater angles will also allow for drainage of the liquid contents from the sharps container. An alternative would be to rotate the sorting surface and the sharps container about axis 28 in arc 112 and then rapidly back in an opposite direction in order to jostle the contents of the sharps container, so that any liquid contents trapped therein would be allowed to escape and drain into waste bin 44.

In order to enable the liquid contents to drain, the sorting surface does not seal against the top of the sharps container, and instead forms opening 42 between the top of the sharps container and the sorting surface. Opening 42 is sufficiently large to only enable the liquid contents to be drained from the sharps container, but not so large that reprocessable or non-reprocessable medical devices are able to slide through the opening and into the waste bin.

Figure 7:
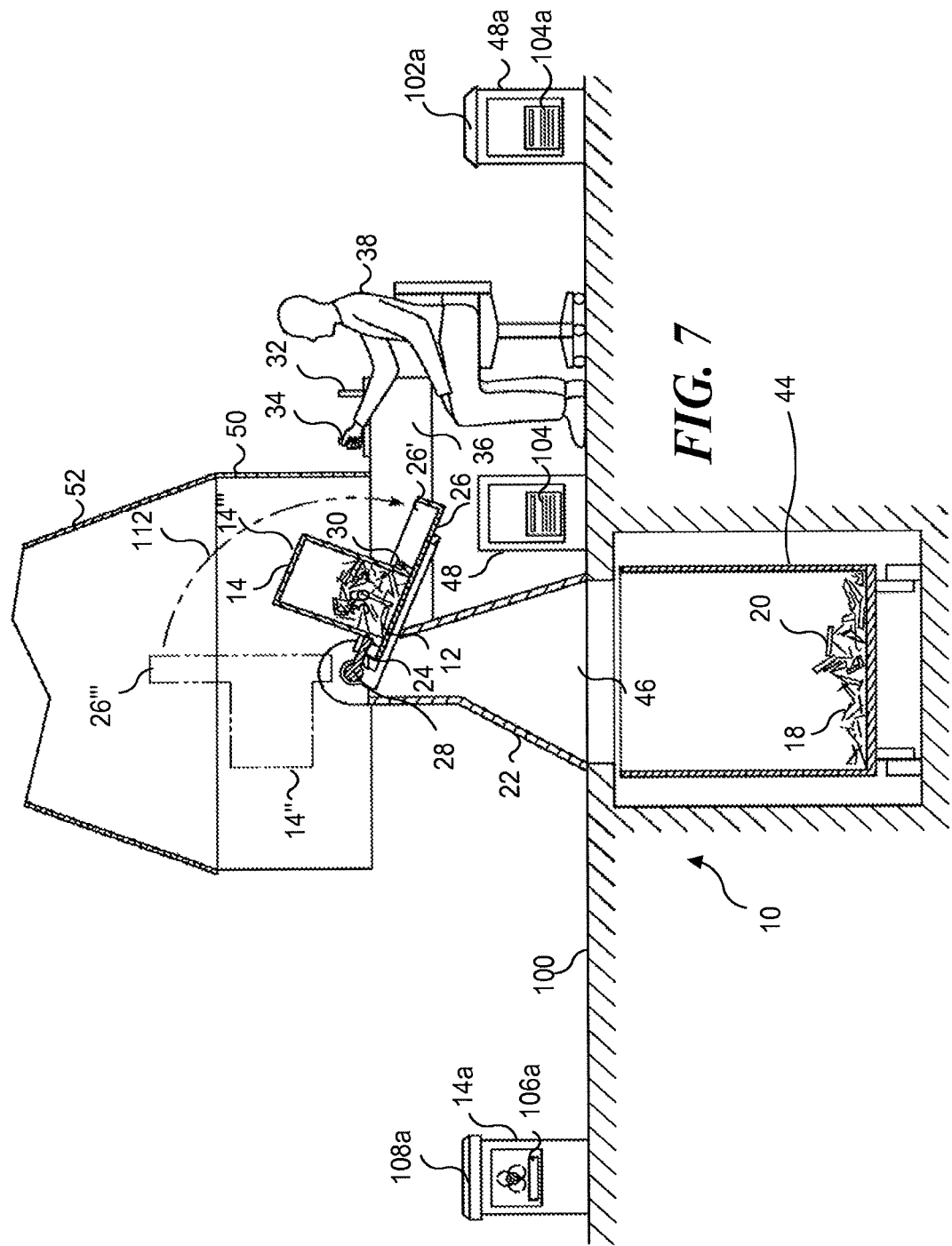
FIG. 7 is a schematic plan view showing the sharps container and the sorting surface manipulated into a position to dump the contents of the sharps container onto the sorting surface to facilitate sorting.

Once the operator has observed that there does not appear to be any more liquid contents 40 draining from the sharps container, the operator will then further rotate both the sorting surface and the sharps container as a unit into the respective positions shown in FIG. 7. Thus, the sharps container and the sorting surface continue rotating around axis 28 through arc 112 until the sharps container is substantially fully inverted in a position 14''' and the sorting surface is substantially in its initial position 26'. Medical devices and medical waste should be thus dumped onto sorting surface 26 from inside sharps container 14.

Figure 8:
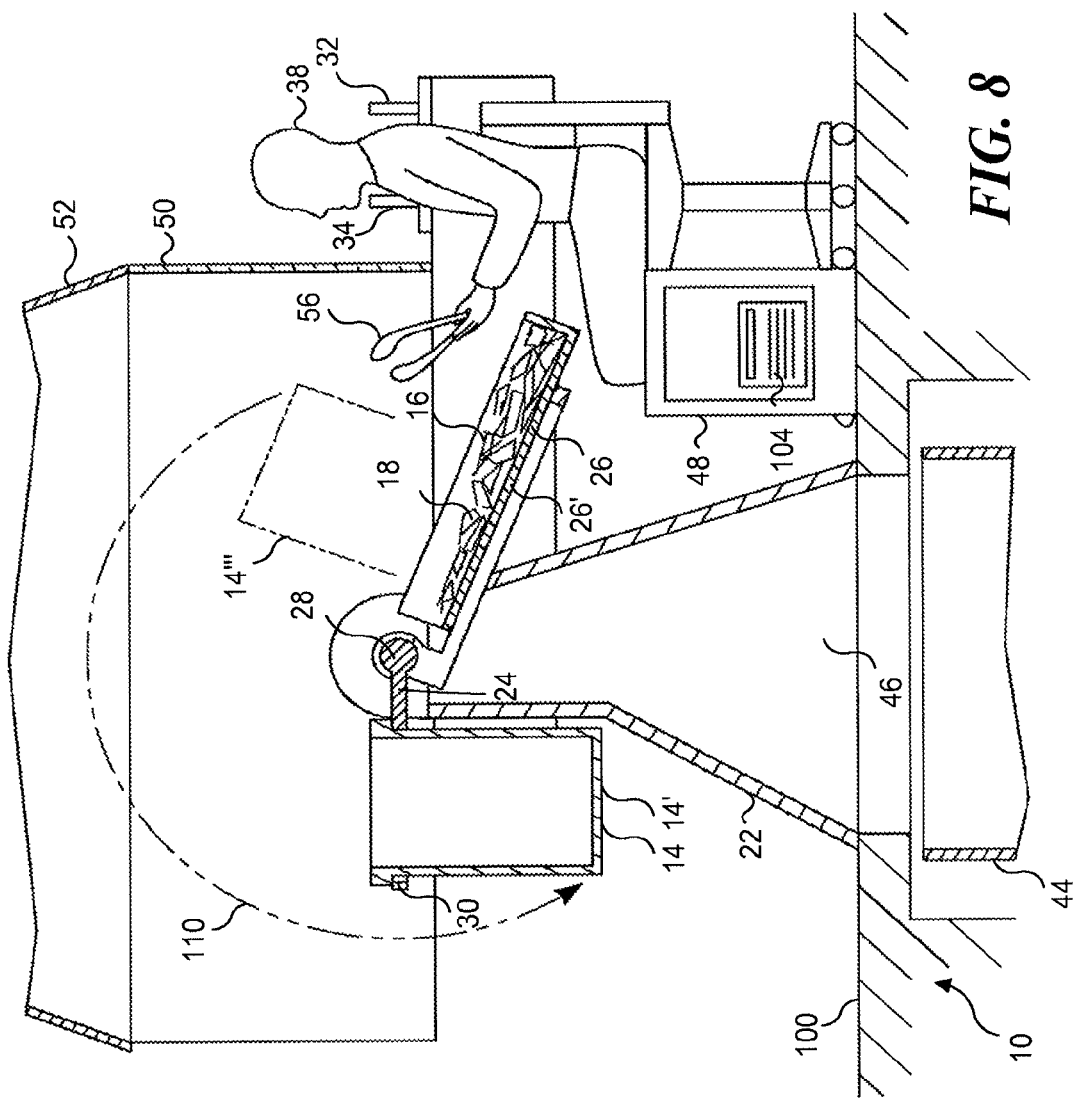
FIG. 8 is a schematic plan view showing an operator sorting the contents of the sharps container that have been deposited onto the sorting surface.

At this point, operator 38 will engage main crank 34 so that sharps container 14 is disengaged from the sorting surface and rotated about axis 28 along arc 110 in a controlled manner, as shown in FIG. 8. As sharps container 14 is rotated about axis 28, any remaining contents of the sharps container should be deposited onto the sorting surface, which is sized so as to contain all of the contents of the sharps container. Shield 50 is useful for protecting operator 38 from being splashed by residual liquid contents that were not disposed of earlier, that may escape from the sharps container or be aerosolized as the contents are upended onto the sorting surface. In the event that some of the total contents cling to the inside of the sharps container, the operator will manually remove these contents with tongs 56 (or other appropriate implement) and move the contents onto the sorting surface.

Once the sharps container has completed its rotational movement, it will be at its loading position 14', as shown in FIG. 8. Sharps container 14 may now have lid 108 replaced, and latch 30 can be opened to enable the sharps container to be removed from brackets 24. Sharps container 14 can now be put into a queue for cleaning and disinfecting so that it may be reused in a medical care facility. Operator 38 will then sort through the reprocessable medical devices 16 and the non-reprocessable medical devices 18 in the sorting tray. Using tongs 56, operator 38 can reach between shield 50 and the top of sorting surface 26 and remove any reprocessable medical devices that may be resterilized, reused, and repackaged, and thus available for reuse. The operator will then place the reprocessable medical devices into receptacle bin 48 that is disposed near the operator.

As shown in FIG. 8, the shield that is in front of the operator protects the operator from contaminants and is transparent, so that the operator can see the medical devices on the sorting surface. There is sufficient clearance between the sorting surface walls and the bottom of the shield, for the operator to reach under the bottom of the shield and the top of the front wall on the sorting tray and freely sort through the medical devices and wastes disposed on the sorting surface without being obstructed. In the alternative, the shield can be designed so that a portion of it can be repositioned and moved out of the way, in order to enable the operator better access to the sorting surface.

When operator 38 sees a reprocessable medical device that is suitable for cleaning and reuse, operator 38 will then place that reprocessable medical device into receptacle bin 48. The operator may use tongs 56 or any other implement that enables the operator to safely and securely grasp the medical device, since as mentioned above, the sharps container is intended to contain devices that are sharp, and therefore the operator could be injured by a sharp medical device if not properly handled. Some of the medical devices that may be reused and deposited in receptacle bin 48 include, but are not limited to the following: trocars, laparoscopic devices, endoscopic devices, cutters, staplers, graspers, harmonic scalpels, burrs, blades, oxisensors, compression sleeves, catheters, bits, and saws.

Once the operator has retrieved all of the reprocessable medical devices and placed them into receptacle bin 48, the types of medical devices left behind on the sorting surface that cannot be reused include, for example: hypodermic needles, syringes with and without needles attached, scalpels, pipettes, blood vials, broken glassware such as flasks, beakers, and specimen tubes, culture dishes, IV tubing, IV bags contaminated with visible blood, and exposed dental wires. Other types of non-reprocessable medical devices and medical waste can also be left on the sorting surface.

Figure 9:
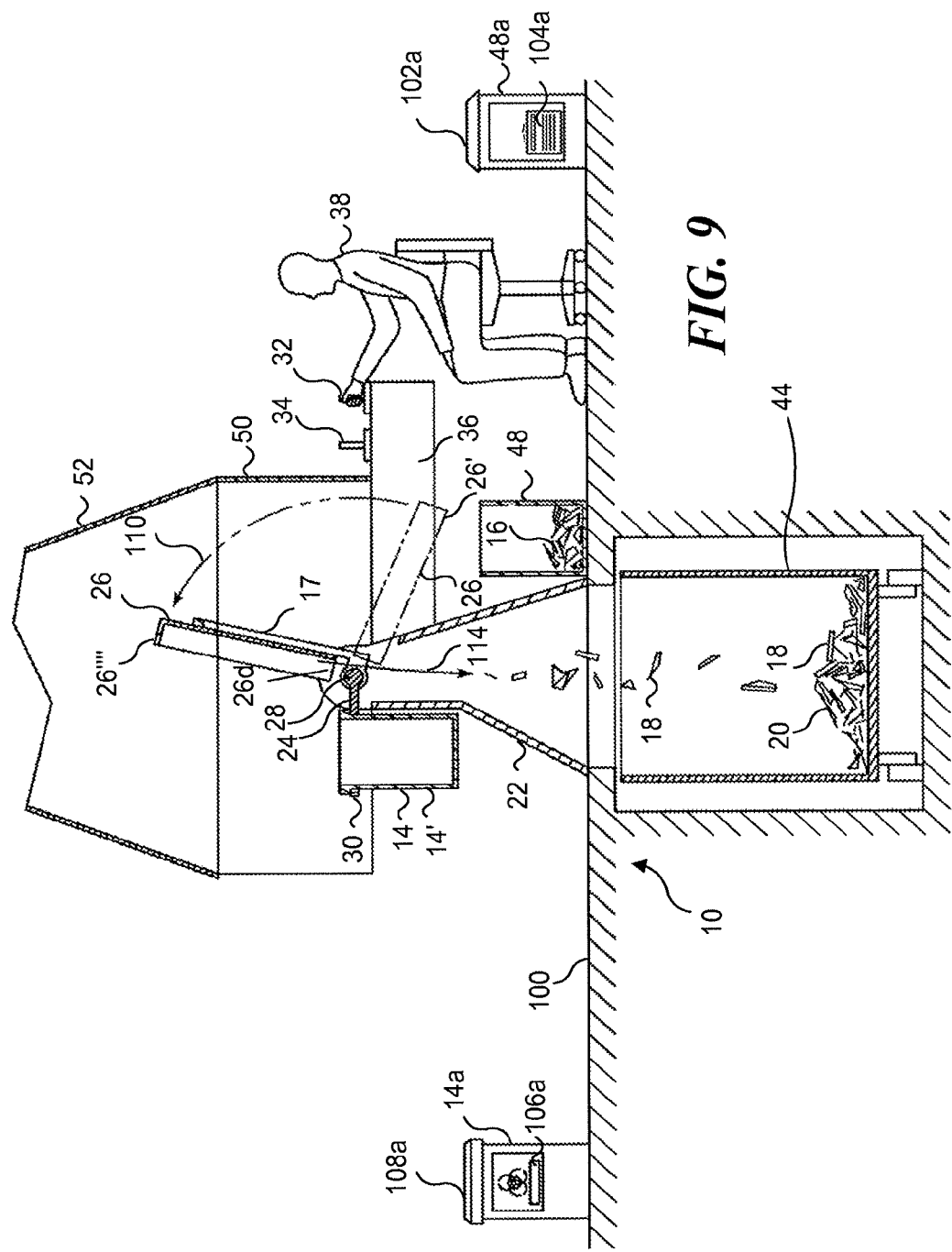
FIG. 9 is a schematic plan view showing the operator manipulating the recovery device so that the non-reprocessable medical devices and other medical wastes that are left on the sorting surface after the sorting routine is completed are deposited into a waste bin.

Turning now to FIG. 9, operator 38 will engage hand crank 32 to rotate sorting surface 26 about axis 28 in arc 110 so that the sorting surface is in a partially inverted position 26''''. Non-reprocessable medical devices 18 that were left behind on the sorting tray will then start to freely fall into waste bin 44, under the force of gravity, as indicated by dash line 114. The non-reprocessable medical devices will exit the sorting tray through opening 26d. Because of the nature of the medical waste and its associated fluids, it is very possible that some non-reprocessable medical devices may occasionally stick to the sorting surface, e.g., in residue that is formed thereon. At this point, operator 38 may manually remove these non-reprocessable medical devices and medical waste using tongs 56 or some other implement suitable for grasping moving the non-reprocessable medical devices and medical waste into waste bin 44. The sorting surface is then returned to its original position 26'.

Another sharps container may be loaded into the recovery device if the receptacle bin is not full, as shown in FIG. 9. For example, if a heart surgery department of a specific hospital has submitted another sharps container to be sorted, as well as the sharp container that was just sorted, this additional sharps container may be processed and its reprocessable medical devices placed in receptacle bin 48 until the receptacle bin is full. If receptacle bin 48 is full of reprocessable medical devices, receptacle bin 48 can then also be queued for reprocessing. The receptacle bin may have its contents cleaned, resterilized, or repackaged, and made ready for reprocessing at the recycling facility, in accordance with government regulations, so that it can be shipped by a common carrier without being labeled as biohazard infectious waste, which substantially reduces the cost of its transportation. In the alternative, the receptacle bin may be sealed and shipped to a remote facility for cleaning, resterilization, and repackaging for reuse of the contents.

Recovery Processing System

Another exemplary embodiment provides a safe, efficient, and continuous method and system whereby the contents of the sharps container is processed for reuse by utilizing a plurality of processing stations and one or more conveyors. Each processing station performs an operation on either the sharps container or at least a portion of its contents, and a conveyor guides the sharps container or at least a portion of its contents on at least one path into and/or out of the processing stations. However, it will be appreciated that alternatives to a conveyor can instead be used for conveying either the sharps containers or their contents between processing stations. For example, conveyance may be performed in a manual manner between one or more of the processing stations, e.g., using trays or carts that are manually carried or pushed.

The exemplary embodiments of the recovery processing system integrate the functionality of recovery device 10 into a processing station and couple it with one or more conveyors or other automated/manual conveyances to provide for continuous and complete processing of the contents of the sharps containers in a safe and efficient manner.

The recovery device as described above may be used in this continuous processing system and can be combined with additional processing stations to individually and successively perform other operations, such as scanning the contents, disposing of the contents, disinfecting the contents, and sorting the contents, of the sharps containers. Opening the sharps container is also made possible with the recovery processing system approach. Although one sharps container may be engaged in processing by recovery device 10 at one processing station, another sharps container may be engaged in being disinfected at a different processing station, while yet another sharps container is being opened at still another processing station. This recovery processing system is especially useful for processing multiple sharps container during a defined interval.

Figure 10A:
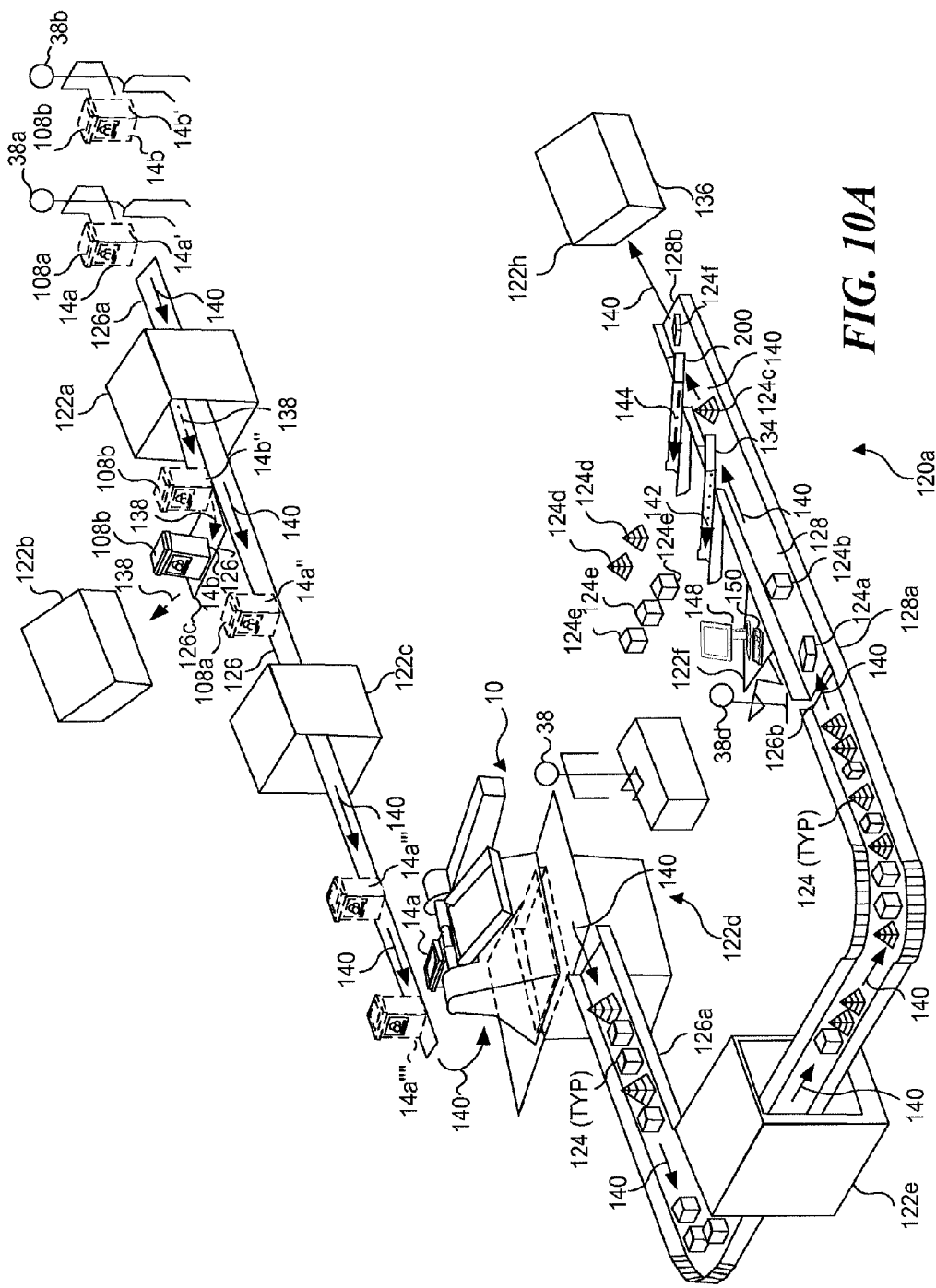
FIG. 10A is an overall isometric view of an exemplary embodiment of the continuous recovery processing system that is used to separate SUDs that can be cleaned and reused from all other medical waste that should be destroyed, where SUDs are contained in a sharps container.
Figure 10B:
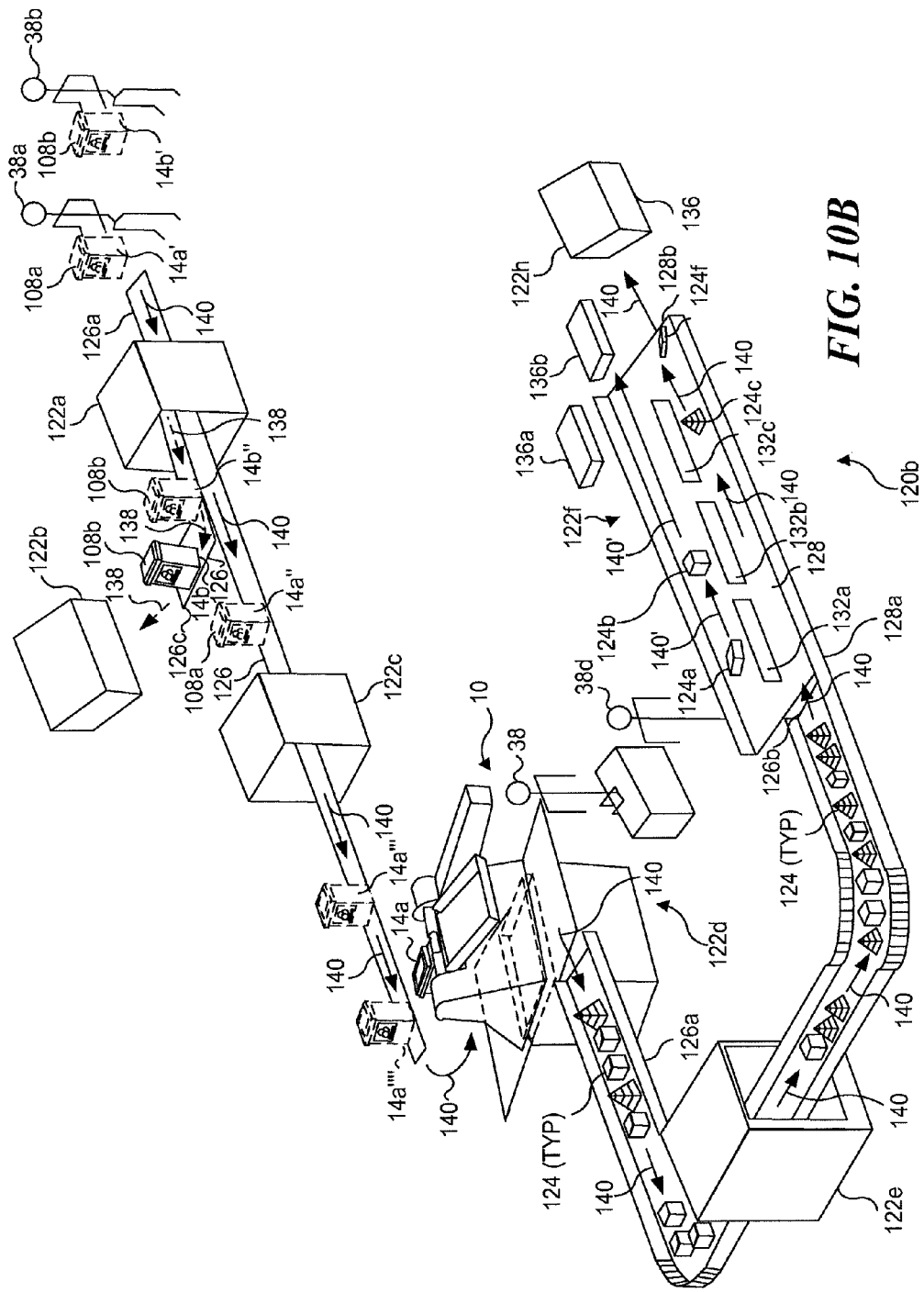
FIG. 10B is an overall isometric view of a different exemplary embodiment of the continuous recovery processing system.
Figure 10C:
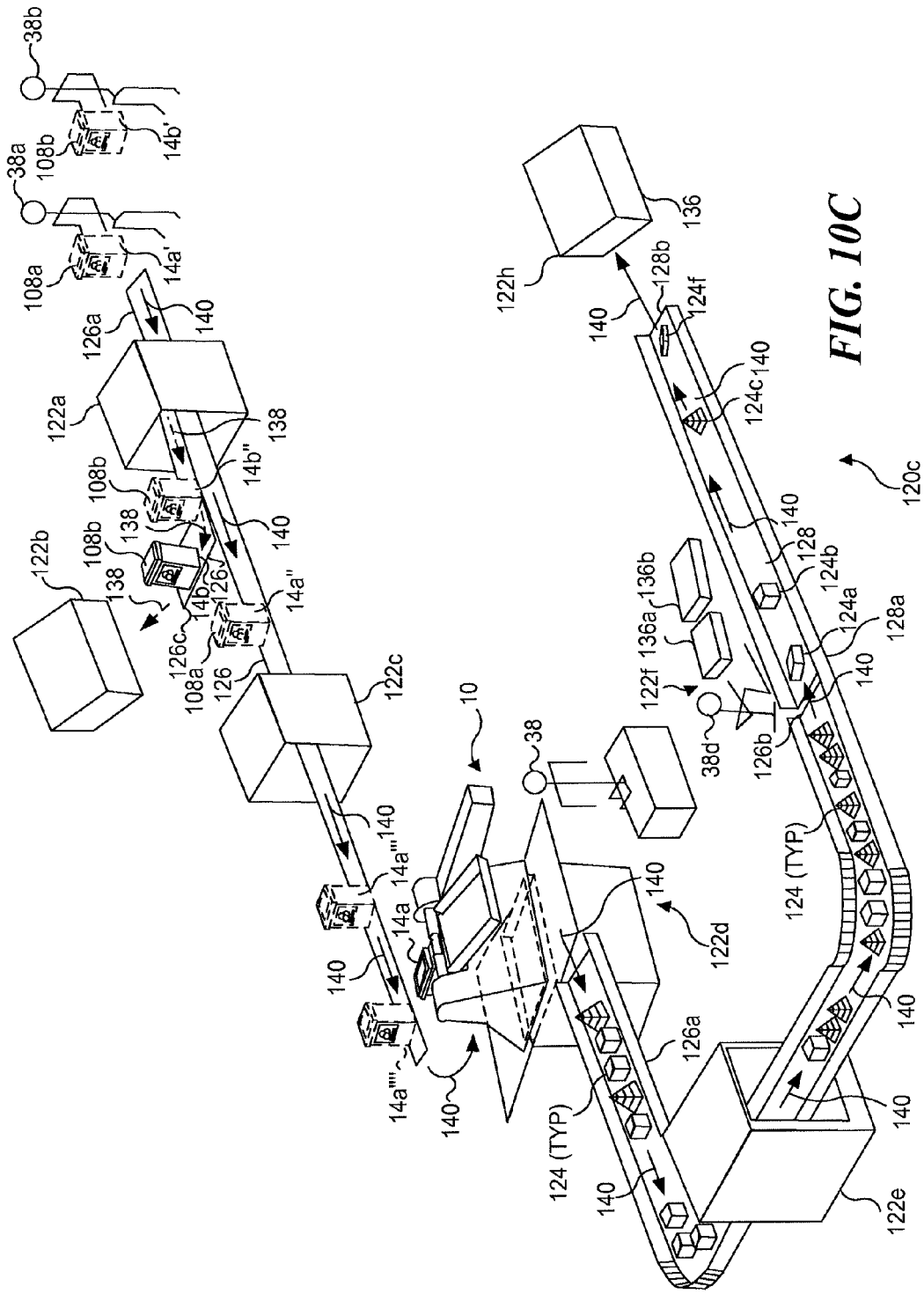
FIG. 10C is an overall isometric view of yet another exemplary embodiment of the continuous recovery processing system.

FIG. 10A, FIG. 10B and FIG. 10C are isometric views of three exemplary embodiments, of a recovery processing system 120a, a recovery processing system 120U, and a recovery processing system 120c, respectively. The recovery system enables continuous recovery of reprocessable medical devices from sharps containers that contain non-reprocessable medical devices and other medical waste that should be disposed of permanently. The recovery system is a continuous rather than a batch process, because operations are simultaneously performed on either a plurality of sharps containers or a portion of their contents at successive processing stations, as described below. A determination is made at each processing station as to the next processing station that the sharps container or at least a portion of its contents will be directed until the sharps container and its contents are fully processed.

As illustrated in FIG. 10A, FIG. 10B and FIG. 10C, the exemplary embodiments of recovery processing system 120a, recovery processing system 120b, and recovery processing system 120c include a detecting processing station 122a, an initial disposal processing station 122b, an initial disinfection processing station 122c, a separation processing station 122*d*, a final disinfection processing station 122*e*, a sorting processing station 122*f*, a final disposal processing station 122*h*, a first conveyor 126, and a second conveyor 128. Each processing station is configured to perform at least one operation on a sharps container and/or a portion of its contents. However, as discussed below, recovery processing system 120*b* and recovery processing system 120*c* illustrate alternative configurations for the sorting processing station 122*f*.

Generally, the detecting processing station is configured to analyze physical properties of the contents of a sharps container. This step may determine that a current sharps container does not include any reprocessable medical device, but only includes non-reprocessable devices and/or medical wastes and should be destroyed. The initial disposal processing station is configured to respond to the presence of either a sharps container or contents of the sharps container that have been conveyed to the initial disposal processing station, so that the sharps container or its contents should be destroyed because there are no potentially reprocessable medical devices present in the sharps container. In other words, the physical analysis of the sharps container and its contents at the prior processing station, the detector processing station, revealed that this sharps container and its contents should be targeted for disposal. In the exemplary embodiment, the initial disposal processing station is simply configured as a holding area for all sharps containers or contents that were conveyed to the initial disposal processing station, and these sharps container are thus earmarked for transport to another facility for destruction. Those skilled in the art will realize that the initial disposal processing station could be configured to perform on-site disposal of the sharps container and its contents. For example, it could include a medical waste approved incinerator.

The initial disinfection station either performs a preliminary disinfecting or sterilizing of the contents of the sharps containers in order to protect downstream operators of the recovery processing system from bio-hazardous waste.

The separation processing station (i.e., recovery device 10 shown without vent 52 for clarity) is configured to empty the contents of the sharps container onto the sorting surface and enable sorting potentially reprocessable medical devices from those medical devices that do not have any reuse and medical waste.

The final disinfection processing station is used to perform final disinfecting and cleaning of the variety of potentially reprocessable medical devices that were identified in the separation processing station. The sorting processing station is configured to sort the potentially reprocessable medical devices into reprocessable medical devices and non-reprocessable medical devices. In addition, this process station is also configured to enable the reprocessable medical devices to be sorted into groups by the type of medical device, so that they may then be packaged accordingly for reuse. The final disposal processing station is configured to include a first receiver container 136 for holding all of the medical devices that were finally identified as being non-reprocessable. As in the initial disposal processing station, these non-reprocessable devices are thus earmarked for destruction, either locally or after being transported to another facility. However, those skilled in the art will realize that the final disposal processing station could be configured to actually perform on-site disposal of the non-reprocessable medical devices. Although it is not included in this exemplary embodiment as a separate processing station, an opening processing station is configured to provide access to the contents of the sharps container by cutting open the sharps container. Conventional sharps containers are not designed to have their top removed and unless newer sharps containers are developed that are designed to be opened as a processing facility as described herein, it will be necessary to cut the sharps containers to remove their top and access their contents.

First conveyor 126 includes a first proximal end 126*a*, a first distal end 126*b*, and a second distal end 126*c*. In general, the first conveyor is configured to convey either a sharps container or at least a portion of its contents into and out of a processing station via one or more routes, because a determination made at a processing station may dictate that the sharps container be directed to one of two or more different processing stations or destinations, along different paths. Although described in greater detail below, in the exemplary embodiment, the first conveyor conveys sharps container 14*a* from first proximal end 126*a* of the first conveyor into and out of not only detector processing station 122*a* but also initial disinfection processing station 122*c* along the path indicated by a solid-line arrow 140. In contrast, the first conveyor conveys sharps container 14*b* from first proximal end 126*a* of the first conveyor into and out of detector processing station 122*a* along the path indicated by solid-line arrow 140. But then, the first conveyor directs sharps container 14*b* to second distal end 126*c*, i.e., to initial disposal processing station 122*b* along the path indicated by a dash-line arrow 138.

Second conveyor 128 includes a proximal end 128*a* and a distal end 128*b*. Second conveyor 128 is configured to convey potentially reprocessable medical devices and non-reprocessable medical devices derived from the potentially reprocessable medical devices along a plurality of routes. In the exemplary embodiment, these routes include a path indicated by a dotted-line arrow 142 (FIG. 10A) and a single dashed and dotted line arrow 144. The second conveyor also includes a first diverter 134 and a second diverter 200. The first diverter and the second diverter are disposed proximate the distal end of second conveyor 128 and are shown in a deflected position such that each diverter extends out across a portion of second conveyor 128. In this manner, each diverter will deflect or divert a reprocessable medical device to follow a path as indicated by a dotted line arrow 142 or a single dash-dot line arrow 144, respectively. If a potentially reprocessable medical device has been identified as not reprocessable, the first and second diverter will not be deflected and thus, the non-reprocessable medical device will follow a path indicated by solid-line arrow 140 where it is deposited in a receiver container 136 and eventually destroyed.

Second conveyor 128 is also configured such that its speed can be set to be different than the speed of the first conveyor. Thus, the second conveyor can be operated at an increased speed as compared to the first conveyor. The increased speed aids in spreading out the potentially reprocessable medical devices as they are transferred from the first conveyor to the second conveyor. This increased spacing between the medical devices aids the operator in sorting the potentially reprocessable medical devices from the non-reprocessable medical devices, because the devices become easier to identify and the spacing allows the diverter more time to operate. If the medical device is reprocessable, it will be directed to a group of similar type medical devices. If the medical device is non-reprocessable, it will be directed to final disposal processing station 122*h*. The decisions regarding whether a medical device is reprocessable should be made before the second conveyor conveys the next potentially reprocessable medical device into proximity of the operator, since failure to make a timely decision will result in the sorting process failing. The operator will thus likely have an option to pause the first and second conveyors if necessary to take a break or avoid getting behind the arrival times of successive medical devices to be evaluated.

Those skilled in the art will realize that multiple conveyors can be configured to convey sharps containers or their contents along additional paths, and thus, other embodiments are not limited to include only the first conveyor and the second conveyor. Furthermore, it is not necessary that the speed of the first and second conveyor be different. For example, another exemplary embodiment could be configured with three conveyors, wherein all three conveyors have a selectively variable speed or the same fixed speed.

Figure 11:
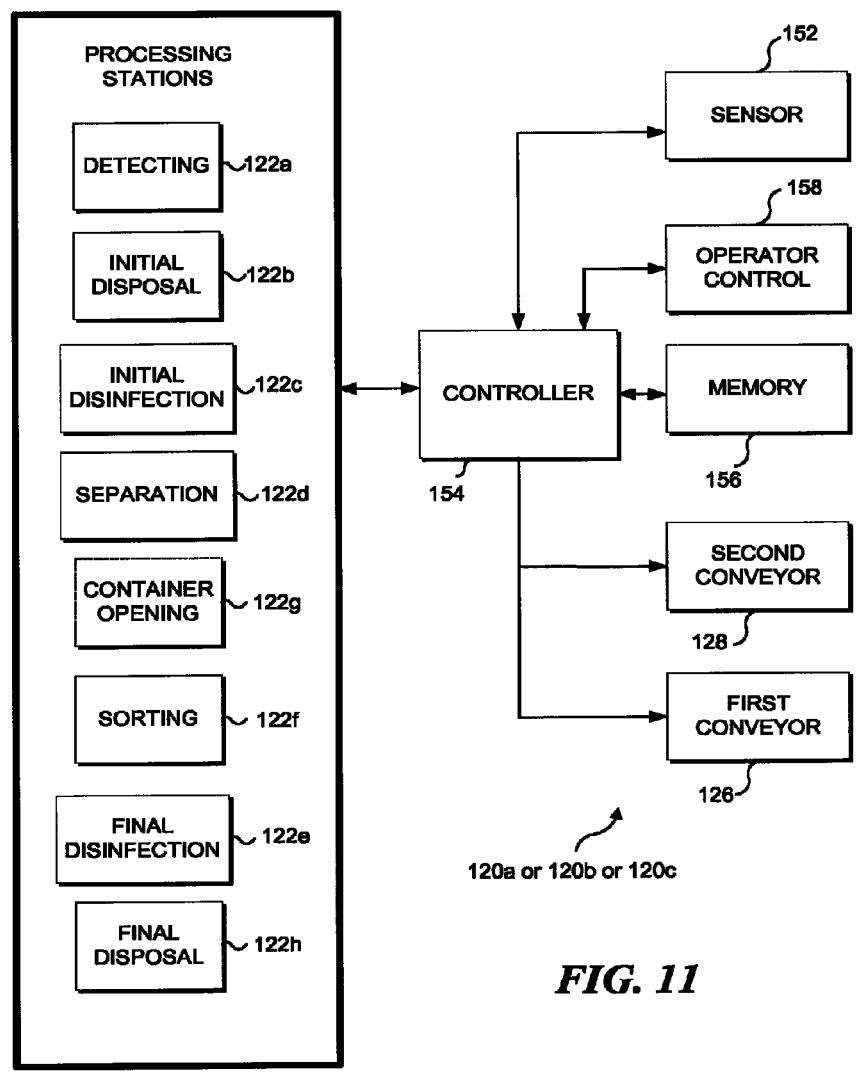
FIG. 11 is a schematic block diagram of an exemplary embodiment recovery system configured to continuously process sharps containers in order to recover reprocessable medical devices that can be processed for reuse.

FIG. 11 is a schematic block diagram of recovery processing system 120a, recovery processing system 120b and recovery processing system 120c that illustrate additional components of the recovery processing system. Also included are a sensor 152, a controller 154, a memory 156, and an operator control 158. Sensor 152 is disposed within each processing station and is configured to sense when either a sharps container or a portion of its contents is disposed within the processing station at a predefined location where an operation can be performed on the sharps container or its contents. The sensor may also be configured to determine when an operation has been completed. Suitable exemplary sensors include optical, magnetic, and capacitive sensors. Controller 154 is coupled bi-directionally to memory 156 that includes both random access memory (RAM) and read only memory (ROM). Memory 156 is used for storing data and machine instructions that control the functionality of the processing stations and operation of at least one of the first conveyor and the second conveyor. Specifically, the controller can pause or stop the first conveyor and/or second conveyor such that an operation can be performed on either a sharps container or a portion of its contents. The controller must then restart at least one of the first conveyor and second conveyor after such an operation has been performed, and select an appropriate path (if more than one path from a processing station is provided) as indicated, for example, by one of solid-line arrow 140, dotted-line arrow 142 and single dash-dot line arrow 144 that the sharps container and a portion of its contents will follow after an operation has been performed. The controller must enable either the sharps container or at least a portion of the contents of the sharps container to be transferred from the first conveyor to the second conveyor (in this exemplary embodiment). Also, the controller might be required to either increase or decrease the speed of one or the first and second conveyors, as necessary to control the spacing between the potentially reprocessable medical devices in order to facilitate identification of the medical devices as reprocessable and for final sorting of reprocessable medical devices.

Operator control 158 is in communication with controller 154 and preferably, one of a plurality of different operators can use operator control 158 to manually intervene in the operation of the recovery processing system. For example, an operator at a processing station may desire to stop, start, pause or accelerate one of the first conveyor and the second conveyor. The operator may also make the determination that one of the sharps container and a portion of its contents is to be directed to a specific other processing station and using operator control 158 specify a particular path that will be used to convey a sharps container or a portion of its contents to the specific processing station. For example, an operator may determine that a disinfection cycle needs to be repeated on certain sharps containers or their contents, thus overriding the further automatic processing until the disinfection cycle is repeated. Or an operator may initiate removal of the top of a sharps container by manual intervention, if the automated process does not successfully complete the task.

Also shown in FIG. 11 is an optional container opening processing station 122g. In an exemplary embodiment, the functionality of the container opening processing station is incorporated into the initial disinfection processing station and the separation processing station. But those skilled in the art will realize that recovery processing system 120a, 120b, or 120c could be configured with a processing station devoted to opening of the sharps container.

Detecting Processing Station Components

FIG. 12 illustrates the various components with which the different processing stations may be configured. Detecting processing station 122a is configured to include at least one of a scale 202, a detector 204, an imager 206, and a first display 208 to enable it to perform a physical analysis operation to determine the contents of the sharps container. Scale 202 is employed to weigh a sharps container. The weight is then conveyed to an operator via the first display. In addition, detector 204 is utilized to determine a metal or liquid content and a radioactivity level within a sharps container. This information is also then conveyed to the operator and present on the first display. Size information of at least a portion of the contents of the sharps container is also provided via imager 206, which scans the contents of the sharps container and provides measurement data to the operator on the first display. The imager may be an x-ray scanner or an ultrasound unit. Based on these data, a trained operator can make one of several determinations. Sharps containers originating from various departments within a medical facility will contain various contents associated with those departments. Numerous trials opening all sharps containers have yielded data that are key indicators of sharps containers likely to include reprocessable devices. For example, sharps containers that weigh more than a certain threshold and are known to originate in a department that does not use reprocessable devices of the type targeted can be identified as unlikely to contain reprocessable devices. Similarly, decisions about the likely content can be made about sharps containers based on their liquid content, radioactivity, and metal content. Scanning sharps containers optically or with x-ray or ultrasound yields image patterns that may correspond to the shapes of commonly reprocessed medical devices. To illustrate, if the data indicates that most of the content is liquid, the operator may conclude that the sharps container should not be opened because there are likely no reprocessable medical devices present and the sharps container should instead be forwarded to the disposal processing station. Similarly, if the data indicates a high level of radioactivity, the operator may also conclude that the sharps container needs to be destroyed, because reprocessable medical devices are not likely to be found in such containers, or for safety reasons, the container should remain closed. Conversely, if there is substantial metallic content indicated by the data, this information coupled with the size of the components comprising the content may indicate to the operator that potentially, reprocessable medical devices are present and that processing of the sharps container should proceed. If the weight of the sharps container falls into a certain range, the operator might conclude that contents are likely to include certain types of reprocessable medical devices that normally weigh more than other types of medical devices. Thus, the operator would know by the weight reading that a sharps container should be further processed.

As described above, each processing station can be controlled by (one or more) operator control 158. Thus, an operator may be manually controlling the entry of a sharps container into a processing unit and may then pause the first conveyor so that a physical analysis is performed on the sharps container. Then, after the operation is completed, the operator should be able to restart the first conveyor. Once the operator determines the next processing station to which the sharps container (or at least a portion of its contents) should be directed, the operator may use operator control 158 to select the path along which the sharps container will be conveyed.

Thus, the operator control is configured to enable the operator to select a route along which the sharps container is directed, toward a selected processing station or destination. The operator control is further configured to activate diverters (not shown) to divert the sharps container, for example, from a path indicated by solid-line arrow 140 (FIG. 10A), to a different path, such as the path indicated by dash-line arrow 138 (FIG. 10A).

In the alternative, memory 156 also includes machine instructions such that the data that is displayed to the operator may be automatically analyzed by software and an automatic determination can be made as to the path or next processing station to which the sharps container or at least a portion of the contents thereof should be directed. The software would also automatically control any diverters or gates to enable the sharps container or medical devices to be diverted to the appropriate processing station or destination.

Initial and Final Disinfection Processing Station Components

The final disinfection processing station and the initial disinfection processing station include at least one of a disinfector and sterilizer 210 and an indicator 212. By providing one of disinfection processes and sterilization processes, the initial disinfection processing station is designed to provide an additional level of safety for operators that may come in contact with the contents of the sharps containers. Thus, the sharps container may be disinfected or sterilized by disinfector and sterilizer 210 that uses ozone, hydrogen peroxide, ethylene oxide, or other chemical steriliant, an electron beam, microwave irradiation, steam, gamma radiation, a vacuum, heat, x-rays, or ultra-violet light directed towards the sharps container and/or its contents. Note, that some of the processes such as the use of ozone, the electron beam, microwave irradiation, gamma radiation, and ultra-violet light can be performed prior to removal of the lid if it is determined that application of these processes reduces the likelihood of operator exposure to bio-contaminants.

Operator control 158 enables an operator to initiate one of these disinfection or sterilizing processes on a sharps container and/or its contents. If configured with indicator 212, when indicator 212 indicates to the operator that the cycle is complete, the operator can enable the first conveyor to convey the sharps container and/or at least a portion of its contents to the next processing station.

Final disinfection processing station 122h performs either disinfection processes and/or cleaning processes on potentially reprocessable medical devices that have been separated from medical waste and non-reprocessable medical devices. The cleaning process employs steam, chemicals, ultrasound, enzymatic cleaners, and/or detergents. Operator control 158 enables an operator to initiate one of the cleaning and sterilizing processes on the potentially reprocessable medical devices. Similarly, indicator 212 is available to indicate to the operator that the process is complete. In the alternative, the final disinfection station may operate automatically in response to a signal from a sensor that determines when potentially reprocessable medical devices are disposed within the final disinfection processing station.

Container Opening Processing Station Components

Container opening processing station 122g also includes a cutting device 214. The cutting device enables removal of the top of a sharps container in order to access the contents. Note that in one exemplary embodiment, the cutting device is integrated into the initial disinfection processing station. The sharps container is secured in place manually or automatically, and when the operator initiates the process, a cutting device is driven to automatically remove the top from the sharps container. In the alternative, sensor 152 may be employed to activate the cutting device in an automated manner.

Separation Processing Station Components

Separation processing station 122d includes sorting surface 26. Sorting surface 26 is used to receive potentially reprocessable medical devices that have been separated from the medical waste of the sharps container, as described above in connection with FIGS. 1-9.

Sorting Processing Station Components

Sorting processing station 122f is configured with a second display 148 and a user interface 150 that are coupled to controller 154. When a potentially reprocessable medical device is conveyed into this processing station, an operator 38d makes a visual determination as to whether the medical device is reprocessable. If so, operator 38d employs a user interface to cause at least one of the first diverter (or gate) or the second diverter (or gate) to divert the medical path used for further processing reprocessable medical devices. The sorting station can also direct a reprocessable medical device along a path designated for other reprocessable medical devices of the same type.

In another exemplary embodiment, as shown in FIG. 10B, in lieu of the second display and the user interface, sorting processing station 122f includes a first rail 132a, a second rail 132b, and a third rail 132c. When potentially reprocessable medical devices arrive in the proximity of operator 38d where they can be identified, operator 38d can manually push or activate an automatic diverter or gate to direct non-reprocessable medical devices along a path indicated by solid-line arrow 140 that is directed towards first receiver container 136 (i.e., a path to one side of the rail). In addition, operator 38d can manually push (or use the control) to direct all reprocessable medical devices to a path indicated by a solid-line arrow 140' that is directed towards a third receiver container 136b. Thus, the reprocessable medical devices will be grouped with other reprocessable medical devices of its type.

In yet another exemplary embodiment, as shown in FIG. 10C, in lieu of the plurality of rails, sorting processing station 122f includes a second receiver container 136a and third receiver container 136b. When potentially reprocessable medical devices arrive in the proximity of operator 38d so that they are able to be identified, operator 38d can, for example, simply use tongs, or otherwise manually transfer the reprocessable medical devices to second receiver container 136a or to third receiver container 136b. Thus, the reprocessable medical devices will be manually grouped with other reusable medical devices of their type. This manual process leaves any non-reusable medical devices following a path indicated by solid-line arrow 140 that is directed towards first receiver container 136, which collects the non-reusable medical devices for disposal.

Method of Use of Recovery Processing System

FIG. 13 illustrates the logical steps implemented in connection with the continuous process of the sharps container in the exemplary embodiment of recovery processing system 120a of FIG. 10A. From a start step 162, a step 164 provides for loading a sharps container onto the distal end of first conveyor 126. For example, sharps container 14a (FIG. 10A) is being held by an operator 38a and is shown in an initial position 14a' in which it is about to be loaded onto first conveyor 126, while a sharps container 14b (FIG. 10A) is being held by an operator 38b, in a position 14b', so that it can next be loaded onto the first conveyor. A step 166 then provides for directing sharps container 14a along a path to detecting processing station 122a. Next, a step 168 provides for analyzing or evaluating the contents of the sharps container so that a decision can be made as to whether the sharps container should be further processed. This analysis is based on, for example, data taken from the weight of the sharps container and its liquid and metal and radioactive and imaging content, as explained above. A decision step 170, then provides for determining whether the sharps container should be opened, based on the analysis of the contents. If the answer is "yes," sharps container 14a is caused to be conveyed out of detection processing station 122a, as shown at a position 14a".

In this case, it has apparently been determined that the sharps container should be further processed because it has been directed to initial disinfection processing station 122c (i.e., it has not been routed to the initial disposal processing station). In contrast, in decision step 170, it was determined that sharps container 14b should not be further processed (i.e., the answer in this decision step was "no"). Sharps container 14b has thus been directed out of the detector processing station and towards second distal end 126c of the first conveyor, as shown at a position 14b", and is being routed to initial disposal processing station 122b, as provided in a step 190. A step 198 then illustrates that the recovery process for sharps container 14b is done.

Note that a lid (or top) 108b of the sharps container is still in place, because this sharps container was never processed through the container opening processing station. Instead of sharps container 14b being conveyed along the route indicated by dash-line arrow 140, it has been directed along the route indicated by dash-line arrow 138 and its processing is complete (other than being destroyed).

Sharps container 14a continues through the processing recovery system. A step 172 provides for directing the sharps container to initial disinfection processing station 122c. At this point, a decision step 174 provides for determining whether the top of the sharps container should be removed. If the answer is yes, i.e., that the top of the sharps container should be removed, a step 176 provides for removing the top using the cutting device. Then a step 178 provides for the sterilization or disinfection of the sharps container to take place with the top in place. If the answer is no, i.e., that the top of the sharps container should not be removed, the results of decision step 174 provides that the contents of the sharps container be disinfected or sterilized in a step 178. Note that some of the sterilization and disinfection processes can be performed without removal of the top. For example processes such as microwaving, steaming, gamma radiation, and electron beam processes can be performed on the sharps container without having the top removed. Due to the analysis of the contents at the detector processing station, the operator may determine visually from the data or the software may automatically determine that one or more of these disinfection and sterilization processes should be applied prior to any removal of the lid in order to provide more protection for an operator and to protect the operator from potential exposure to biohazardous waste.

After the sterilization and disinfecting processes are performed, a step 180 provides for directing the sharps container to the separation processing station. A decision step 182 determines whether the top has been removed. If it is determined that the sharps container top has been removed, a step 186 provides for separating potentially reprocessable medical devices from medical waste. Note that this step is described in detail in FIGS. 1-9.

To summarize, the contents of a sharps container are here categorized as potentially reprocessable medical devices, which includes both reprocessable and non-reprocessable medical devices, and other contents, i.e., medical waste. The medical waste is disposed of at this station, while the potentially reprocessable medical devices undergo an additional sorting at a subsequent processing station to separate the potentially reprocessable medical devices into reprocessable medical devices and non-reprocessable medical devices. If it is determined that the sharps container top has not been removed (i.e., the answer to decision step 182 is "no") then the cutting device will be used to automatically remove the top of the sharps container in a step 184. After this step, the process of separating potentially reprocessable medical devices from the medical waste (at a step 186) then proceeds.

In the exemplary embodiment illustrated in FIG. 10A, sharps container 14a had its top removed while at the initial disinfection processing station, as shown at a position 14a''' and at a position 14a''''. A step 188 provides for sharps container 14a to be directed to final disinfection processing station 122e. However, at this point in the process, a sharps container is not being directed along the first conveyor, but the contents of the sharps container are being directed along the first conveyor. So, it is not a sharps container at this point that is going to be disinfected and cleaned at the final disinfection processing station. Instead, potentially reprocessable medical devices will be disinfected and cleaned at the final disinfection processing station. As illustrated in FIG. 10A, for example, potentially reprocessable medical devices 124 have been separated from the medical waste in sharps container 14a and are being directed along the path indicated by solid-line arrow 140 to final disinfection processing station 122e. The operator may choose from a program menu to activate one or more selected disinfection and cleaning processes, using operator control 158, as indicated in a step 192. Sensor 152 may also be employed to enable the potentially reprocessable medical devices to be run through on a continuous basis or the sensor may be used to automatically stop and start these processes.

When these processes are complete, the potentially reprocessable medical devices continue to be directed along the path indicated by solid-line arrow 140 towards sorting processing station 122f (FIG. 10A) and as indicated by a step 194. In order to aid in the sorting process, the potentially reprocessable medical devices are transferred from first distal end 126b of the first conveyor to proximal end 128a of the second conveyor. Prior to the transfer of potentially reprocessable medical devices to the second conveyor, there is very little space between the potentially reprocessable medical devices on the first conveyor. Because the speed of the second conveyor is greater than the speed of the first conveyor, there is much more space between potentially reprocessable medical device 124a and 124b.

A step 194 provides for sorting the potentially reprocessable medical devices. Thus, an operator must determine whether each potentially reprocessable medical device is either reprocessable or not. Operator 38d in the exemplary embodiment is aided by the use of second display 148 and user interface 150. If the potentially reprocessable medical device is reprocessable, the operator must further determine (from a visual image displayed on the second display or optical recognition software) the type of medical device so that it can be directed to be with other previously sorted medical devices of the same type. For example, as shown in FIG. 10A, potentially reprocessable medical device 124b that is represented by a cubic shape is disposed proximate operator 38d, who identifies it as reprocessable and as being of a specific type of medical device.

As shown by dotted-line arrow 142, the operator has decided that potentially reprocessable medical device 124b is reprocessable and has directed it along a path such that it will be accumulated with the same type of reprocessable medical devices 124e. When potentially reprocessable medical device 124b travels past operator 38d, by making a selection with user interface 150, the operator can activate first diverter 134 to move the medical device along a different path, as indicated by dotted-line arrow 142, which is designated for reprocessable medical devices 124e. For example, if potentially reprocessable medical device 124b is a trocar, it will be diverted and grouped with other trocar medical devices. Similarly, potentially reprocessable medical device 124c will be diverted by second diverter 200 in response to the operator's input, such that the medical device will be grouped with other reprocessable medical devices 124d as it travels along the path indicated by single dash-dotted line arrow 144.

A decision step 196 determines whether the potentially reprocessable medical device has been designated as non-reprocessable. If so, a step 203 provides for directing it to first receiver container 136, and the process is then complete, as indicated in a step 198. If not, the process is also complete at step 198.

As illustrated in FIG. 10A, non-reprocessable medical device 124f is being directed to final disposal processing station. Note that the operator allowed to be conveyed past the first diverter and the second diverter in order to maintain its path towards the receiver container disposed at the distal end of the second conveyor, which is intended for non-reprocessable medical devices.

In the alternative embodiment illustrated by recovery processing system 120b in FIG. 10B, operator 38d in the exemplary embodiment is aided by the use of first rail 132a, second rail 132b, and third rail 132c. If the operator determines that a potentially reprocessable medical device is indeed reprocessable, the operator must push the potentially reprocessable medical device to one side of the rail, either manually or by activating a mechanical diverter or gate. For example, as shown in FIG. 10B, potentially reprocessable medical device 124b that is represented by a cubic shape is disposed proximate to operator 38d who has decided that it is reprocessable and has pushed it to one side of the rail. As shown by solid-line arrow 140', the medical device is now directed along a path such that it will be accumulated with other reprocessable medical devices disposed within third receiver container 136b, which is disposed proximate the distal end of the second conveyor. Similarly, note that potentially reprocessable medical device 124a has also been pushed to one side of the rail such that it will be grouped with other reprocessable medical devices, because it also follows the path indicated by solid-line arrow 140'. Second receiver container 136a can be substituted for third receiver container 136b to ensure that reprocessable medical devices are grouped together by similar type.

Decision step 196 determines whether a potentially reprocessable medical device is non-reprocessable. If so, step 203 provides for directing it to the receiver container, by pushing it to the other side of the rail such that it is conveyed along the path indicated by solid-line arrow 140. In this example, non-reprocessable medical devices 124c and 124f are being directed along the path indicated by solid-line arrow 140 to first receiver container 136. The process is then complete as shown in step 198. If not, the process is also complete at step 198. As illustrated in FIG. 10B, non-reprocessable medical device 124f and non-reprocessable medical device 124c are being directed to final disposal processing station 122h.

In yet another exemplary embodiment illustrated by recovery processing system 120c in FIG. 10C, operator 38d in the exemplary embodiment manually sorts reprocessable medical devices into either second receiver container 136a or third receiver container 136b. If the potentially reprocessable medical device is reprocessable, the operator manually removes the potentially reprocessable medical device from the second conveyor. For example, as shown in FIG. 10C, potentially reprocessable medical devices 124b and 124a that are represented by cubic shapes are disposed proximate operator 38d, who, after determining that they are reprocessable, may then manually remove them to receiver container 136a and receiver container 136b, respectively.

Decision step 196 determines whether a potentially reprocessable medical devices is non-reprocessable. If so, step 203 provides for allowing the medical device to continue along the path indicated by solid-line arrow 140. For example, potentially reprocessable medical devices 124c and 124f, which have been to determined to be non-reprocessable, are being allowed to continue along the path indicated by solid-line arrow 140 to first receiver container 136. Then the process is complete as shown in a step 198. If the medical device is reprocessable, the process is also complete at step 198, since the operator will have manually removed it from the second conveyor. As illustrated in FIG. 10C, non-reprocessable medical devices 124f and 124c are being allowed to continue to the final disposal processing station.

Although the present invention has been described in connection with the preferred form of practicing it and modifications thereto, those of ordinary skill in the art will understand that many other modifications can be made to the present invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. A recovery processing system for medical devices that can be recovered from a sharps container that is processed for reuse, said sharps container including medical devices and medical waste that should be destroyed, said recovery processing system comprising:
 (a) a processing station configured to perform an operation on one of a sharps container and a portion of its contents disposed within the processing station, wherein said operation facilitates recovery of reprocessable medical devices from the sharps container;
 (b) a conveyor configured to controllably convey one of a sharps container and the portion of the contents of the sharps container along a route said route directed one of into and out of the processing station, wherein the conveyor passes through the processing station;
 (c) a sensor that senses when one of the sharps container and the portion of the contents of the sharps container are at least one of the following:
  (i) disposed at a predefined location within the processing station such that an operation can be performed; and
  (ii) have had an operation completed;
 (d) a memory in which machine instructions are stored; and
 (e) a controller coupled to the sensor and the memory, said controller executing the machine instructions stored in the memory such that one of the following functions is enabled:
  (i) the conveyor is stopped;
  (ii) the conveyor is started;
  (iii) the conveyor is paused;

(iv) the speed of the conveyor is one of increased and decreased;

(v) the one of the sharps container and the portion of the contents of the sharps container are transferred to a different conveyor;

(vi) select a route along which one of the sharps container and the portion of the contents of the sharps container are directed; and (vii) perform the operation.

2. The recovery processing system of claim 1, wherein the sensor comprises an optical sensor.

3. The recovery processing system of claim 1, further comprising a first operator manipulative control for enabling one of the following:

(a) control the conveyor;

(b) select the route that said one of the sharps container and the portion of the content of the sharps container follows;

(c) disinfect said one of the sharps container and the portion of the content of the sharps container; and (d) initiate removal of a lid of the sharps container.

4. The recovery processing system of Claim 1, wherein the processing station comprises one of:

(a) a scanning processing station configured to analyze physical properties of the portion of the contents of the sharps container;

(b) a disinfection processing station configured to at least one of sterilize, clean, and disinfect said one of the sharps container and the portion of the contents of the sharps container;

(c) a container opening processing station configured to open the sharps container such that the contents of the sharps container are accessible;

(d) a disposal processing station configured to determine that one of the sharps container and at least some portion of the contents of the sharps container is to be destroyed;

(e) a separation processing station configured to separate the medical devices that can be processed for reuse from medical waste and medical devices that should be destroyed; and (f) a sorting processing station configured to sort the medical devices that can be processed for reuse into a category based upon a type of the medical device.

5. The recovery processing system of claim 4, wherein if the processing station is the scanning processing station, the processing station further comprises at least one of:

(a) a scale that is configured to weigh the sharps container disposed within the processing station;

(b) a detector that detects at least one of a metallic content, a liquid content, and a radioactive content of the sharps container;

(c) an imager that images the contents of the sharps container and determines a size of at least one of the contents of the sharps container; and (d) a display to display a visual image of the contents of the sharps container.

6. The recovery processing system of claim 5, wherein the at least one of the scale, the detector, the imager, and the display are coupled to the controller.

7. The recovery processing system of claim 4, wherein if the processing station is the disinfection processing station, the processing station further comprises at least one of:

(a) a disinfector and a sterilizer to at least one of disinfect and sterilize said one of the sharps container and the portion of the contents of the sharps container; and (b) an indicator that indicates when the disinfection process is completed.

8. The recovery processing system of Claim 7, wherein the indicator, and the at least one of the disinfector and the sterilizer are coupled to the controller.

9. The recovery processing system of claim 4, wherein if the processing station is the container opening processing station, the processing station further comprises a cutting device that cuts the sharps container to facilitate removal of a lid of the sharps container such that the contents are accessible.

10. The recovery processing system of claim 9, wherein the cutting device is coupled to the controller.

11. The recovery processing system of claim 4, wherein if the processing station is the separation processing station, the processing station further comprises a sorting surface to receive the contents of the sharps container.

12. The recovery processing system of claim 4, wherein if the processing station is the sorting processing station, the processing station further comprises at least one of:

(a) a second display to display a visual image of the contents of the sharps container; and (b) a user interface to enable the user to change the route along which one of the sharps container and the portion of the contents of the sharps container is directed.

13. The recovery processing system of claim 12, wherein the second display and the user interface are coupled to the controller.

14. The recovery processing system of claim 4, wherein the conveyor includes at least one diverter disposed proximate the conveyor along the route.

15. The recovery processing system of claim 14, wherein said at least one diverter when activated, changes a route along which said one of the sharps container and the portion of the contents of the sharps container is directed.

16. The recovery processing system of claim 4, further comprising at least one receiver container disposed proximate a distal end of the route along which said one of the sharps container and the portion of the contents of the sharps container is directed such that said one of the sharps container and the portion of the contents of the sharps container is directed into said at least one receiver container.

17. The recovery processing system of Claim 1, wherein the conveyor is configured to convey said one of the sharps container and the contents of the sharps container to a different conveyor.

18. The recovery processing system of Claim 17, wherein the conveyor and the different conveyor run at different speeds.

19. The recovery processing system of claim 1, wherein the conveyor splits into a plurality of paths upon exiting the processing station.

20. The recovery processing system of claim 19, wherein reprocessable medical devices are conveyed on at least one of the plurality of paths, while at least one of medical waste and medical devices that should be destroyed is conveyed on another of the plurality of paths.

* * * * *

UNITED STATES PATENT AND TRADEMARK OFFICE
CERTIFICATE OF CORRECTION

PATENT NO. : 8,522,979 B2
APPLICATION NO. : 13/286976
DATED : September 3, 2013
INVENTOR(S) : Bennett et al.

Page 1 of 1

It is certified that error appears in the above-identified patent and that said Letters Patent is hereby corrected as shown below:

In the Claims

Claim 1, column 24, line 51, delete "route said" and insert -- route, said -- therefor.

Signed and Sealed this
Twenty-sixth Day of November, 2013

Margaret A. Focarino
*Commissioner for Patents of the United States Patent and Trademark Office*